United States Patent
Bardy et al.

(10) Patent No.: US 10,052,022 B2
(45) Date of Patent: *Aug. 21, 2018

(54) SYSTEM AND METHOD FOR PROVIDING DYNAMIC GAIN OVER NON-NOISE ELECTROCARDIOGRAPHIC DATA WITH THE AID OF A DIGITAL COMPUTER

(71) Applicant: Bardy Diagnostics, Inc, Charlotte, NC (US)

(72) Inventors: Gust H. Bardy, Carnation, WA (US); Jason Felix, Vashon, WA (US); Jon Mikalson Bishay, Lexington, KY (US); Ezra M. Dreisbach, Vashon, WA (US)

(73) Assignee: Bardy Diagnostics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,242

(22) Filed: Aug. 21, 2017

(65) Prior Publication Data
US 2017/0340206 A1 Nov. 30, 2017

Related U.S. Application Data

(63) Continuation of application No. 15/420,032, filed on Jan. 30, 2017, now Pat. No. 9,737,211, which is a
(Continued)

(51) Int. Cl.
*A61B 5/0432* (2006.01)
*A61B 5/00* (2006.01)
(Continued)

(52) U.S. Cl.
CPC ............ *A61B 5/0006* (2013.01); *A61B 5/044* (2013.01); *A61B 5/04017* (2013.01);
(Continued)

(58) Field of Classification Search
None
See application file for complete search history.

(56) References Cited

U.S. PATENT DOCUMENTS 3,215,136 A   11/1965  Holter et al.
3,569,852 A *  3/1971  Berkovits .......... A61B 5/04004
                                                330/132
(Continued)

FOREIGN PATENT DOCUMENTS

DE    19955211     5/2001
EP     1859833    11/2007
(Continued)

OTHER PUBLICATIONS 15 of The Hottest Wearable Gadgets, URL http://thehottestgadgets.com/2008/09/the-15-hottest-wearable-gadgets-001253.
(Continued)

*Primary Examiner* — Kennedy Schaetzle
(74) *Attorney, Agent, or Firm* — Patrick J. S. Inouye; Leonid Kisselev

(57) ABSTRACT

In one embodiment, a system and method for providing dynamic gain over non-noise electrocardiographic data with the aid of a digital computer are provided. A time series of a plurality of voltage values that comprises a digital representation of a raw electrocardiography ("ECG") signal recorded by an ambulatory monitor recorder is obtained. One or more segments of the ECG signal is marked as noise, each of the segments including a plurality of the values, based on a difference between a maximum one and a minimum one of the values within that segment. Further segments not marked as noise are analyzed, each of the segments comprising a plurality of the values. A gain factor for all of the values in the analyzed further segments is determined based on the analysis.

20 Claims, 24 Drawing Sheets

Related U.S. Application Data continuation of application No. 15/162,489, filed on May 23, 2016, now Pat. No. 9,554,715, which is a continuation of application No. 14/997,416, filed on Jan. 15, 2016, now Pat. No. 9,345,414, which is a continuation-in-part of application No. 14/614,265, filed on Feb. 4, 2015, now Pat. No. 9,408,545, which is a continuation-in-part of application No. 14/488,230, filed on Sep. 16, 2014, now Pat. No. 9,700,227, which is a continuation-in-part of application No. 14/080,725, filed on Nov. 14, 2013, now Pat. No. 9,730,593.

(60) Provisional application No. 61/882,403, filed on Sep. 25, 2013.

(51) Int. Cl.
 A61B 5/044 (2006.01)
 A61B 5/04 (2006.01)
 A61B 5/0452 (2006.01)
 A61B 5/0408 (2006.01)

(52) U.S. Cl.
 CPC ........ *A61B 5/0432* (2013.01); *A61B 5/04087* (2013.01); *A61B 5/04525* (2013.01); *A61B 5/7203* (2013.01); *A61B 5/7232* (2013.01); *A61B 2560/0456* (2013.01)

(56) References Cited

U.S. PATENT DOCUMENTS

| | | | |
|---|---|---|---|
| 3,699,948 A | 10/1972 | Ota et al. | |
| 3,893,453 A | 7/1975 | Goldberg | |
| 4,123,785 A | 10/1978 | Cherry et al. | |
| 4,328,814 A | 5/1982 | Arkans | |
| 4,441,500 A | 4/1984 | Sessions et al. | |
| 4,532,934 A | 8/1985 | Kelen | |
| 4,546,342 A * | 10/1985 | Weaver | H03M 7/42 341/51 |
| 4,550,502 A | 11/1985 | Grayzel | |
| 4,580,572 A | 4/1986 | Granek et al. | |
| 4,716,903 A | 1/1988 | Hansen | |
| 4,809,705 A | 3/1989 | Ascher | |
| 4,915,656 A | 4/1990 | Alferness | |
| 5,025,794 A | 6/1991 | Albert et al. | |
| 5,107,480 A * | 4/1992 | Naus | H03G 3/3089 360/39 |
| 5,168,876 A | 12/1992 | Quedens et al. | |
| 5,215,098 A * | 6/1993 | Steinhaus | A61B 5/0428 600/509 |
| D341,423 S | 11/1993 | Bible | |
| 5,265,579 A | 11/1993 | Ferrari | |
| 5,333,615 A * | 8/1994 | Craelius | A61B 5/04325 600/509 |
| 5,341,806 A | 8/1994 | Gadsby et al. | |
| 5,355,891 A | 10/1994 | Wateridge et al. | |
| 5,365,934 A | 11/1994 | Leon et al. | |
| 5,392,784 A | 2/1995 | Gudaitis | |
| D357,069 S | 4/1995 | Plahn et al. | |
| 5,402,780 A | 4/1995 | Faasse, Jr. | |
| 5,402,884 A | 4/1995 | Gilman et al. | |
| 5,450,845 A | 9/1995 | Axelgaard | |
| 5,458,141 A | 10/1995 | Neil | |
| 5,473,537 A | 12/1995 | Glazer et al. | |
| 5,483,969 A | 1/1996 | Testerman et al. | |
| 5,511,553 A | 4/1996 | Segalowitz | |
| 5,540,733 A | 7/1996 | Testerman et al. | |
| 5,546,952 A | 8/1996 | Erickson | |
| 5,549,655 A | 8/1996 | Erickson | |
| 5,579,919 A | 12/1996 | Gilman et al. | |
| 5,582,181 A | 12/1996 | Ruess | |
| D377,983 S | 2/1997 | Sabri et al. | |
| 5,601,089 A | 2/1997 | Bledsoe et al. | |
| 5,623,935 A * | 4/1997 | Faisandier | A61B 5/04325 600/509 |
| 5,682,901 A | 11/1997 | Kamen | |
| 5,697,955 A | 12/1997 | Stolte | |
| 5,749,902 A | 5/1998 | Olsen et al. | |
| 5,788,633 A | 8/1998 | Mahoney | |
| 5,817,151 A | 10/1998 | Olsen et al. | |
| 5,819,741 A | 10/1998 | Karlsson et al. | |
| 5,850,920 A | 12/1998 | Gilman et al. | |
| D407,159 S | 3/1999 | Roberg | |
| 5,876,351 A | 3/1999 | Rohde | |
| 5,906,583 A | 5/1999 | Rogel | |
| 5,951,598 A | 9/1999 | Bishay et al. | |
| 5,957,857 A * | 9/1999 | Hartley | A61B 5/7203 600/509 |
| 5,984,102 A | 11/1999 | Tay | |
| 6,032,064 A | 2/2000 | Devlin et al. | |
| 6,038,469 A | 3/2000 | Karlsson et al. | |
| 6,101,413 A | 8/2000 | Olsen et al. | |
| 6,115,638 A | 9/2000 | Groenke | |
| 6,117,077 A | 9/2000 | Del Mar et al. | |
| 6,134,479 A | 10/2000 | Brewer et al. | |
| 6,148,233 A | 11/2000 | Owen et al. | |
| 6,149,602 A | 11/2000 | Arcelus | |
| 6,149,781 A | 11/2000 | Forand | |
| 6,188,407 B1 | 2/2001 | Smith et al. | |
| D443,063 S | 5/2001 | Pisani et al. | |
| 6,245,025 B1 | 6/2001 | Torok et al. | |
| 6,246,330 B1 | 6/2001 | Nielsen | |
| D445,507 S | 7/2001 | Pisani et al. | |
| 6,269,267 B1 | 7/2001 | Bardy et al. | |
| 6,272,385 B1 | 8/2001 | Bishay et al. | |
| 6,298,255 B1 | 10/2001 | Cordero et al. | |
| 6,301,502 B1 | 10/2001 | Owen et al. | |
| 6,304,773 B1 | 10/2001 | Taylor et al. | |
| 6,304,780 B1 | 10/2001 | Owen et al. | |
| 6,304,783 B1 | 10/2001 | Lyster et al. | |
| 6,374,138 B1 | 4/2002 | Owen et al. | |
| 6,416,471 B1 | 7/2002 | Kumar et al. | |
| 6,418,342 B1 | 7/2002 | Owen et al. | |
| 6,424,860 B1 | 7/2002 | Karlsson et al. | |
| 6,427,083 B1 | 7/2002 | Owen et al. | |
| 6,456,872 B1 | 7/2002 | Faisandier | |
| 6,463,320 B1 | 10/2002 | Xue et al. | |
| 6,546,285 B1 | 4/2003 | Owen et al. | |
| 6,605,046 B1 | 8/2003 | Del Mar | |
| 6,607,485 B2 | 8/2003 | Bardy | |
| 6,611,705 B2 | 8/2003 | Hopman et al. | |
| 6,671,545 B2 | 12/2003 | Fincke | |
| 6,671,547 B2 | 12/2003 | Lyster et al. | |
| 6,694,186 B2 | 2/2004 | Bardy | |
| 6,704,595 B2 | 3/2004 | Bardy | |
| 6,705,991 B2 | 3/2004 | Bardy | |
| 6,719,701 B2 | 4/2004 | Lade | |
| 6,754,523 B2 | 6/2004 | Toole | |
| 6,782,293 B2 | 8/2004 | Dupelle et al. | |
| 6,856,832 B1 | 2/2005 | Matsumura | |
| 6,860,897 B2 | 3/2005 | Bardy | |
| 6,866,629 B2 | 3/2005 | Bardy | |
| 6,887,201 B2 | 5/2005 | Bardy | |
| 6,893,397 B2 | 5/2005 | Bardy | |
| 6,904,312 B2 | 6/2005 | Bardy | |
| 6,908,431 B2 | 6/2005 | Bardy | |
| 6,913,577 B2 | 7/2005 | Bardy | |
| 6,944,498 B2 | 9/2005 | Owen et al. | |
| 6,960,167 B2 | 11/2005 | Bardy | |
| 6,970,731 B1 | 11/2005 | Jayaraman et al. | |
| 6,978,169 B1 | 12/2005 | Guerra | |
| 6,993,377 B2 | 1/2006 | Flick et al. | |
| 7,020,508 B2 | 3/2006 | Stivoric et al. | |
| 7,027,864 B2 | 4/2006 | Snyder et al. | |
| 7,065,401 B2 | 6/2006 | Warden | |
| 7,085,601 B1 | 8/2006 | Bardy et al. | |
| 7,104,955 B2 | 9/2006 | Bardy | |
| 7,134,996 B2 | 11/2006 | Bardy | |
| 7,137,389 B2 | 11/2006 | Berthon-Jones | |
| 7,147,600 B2 | 12/2006 | Bardy | |
| 7,215,991 B2 | 5/2007 | Besson et al. | |
| 7,248,916 B2 | 7/2007 | Bardy | |

(56) References Cited

U.S. PATENT DOCUMENTS

| | | |
|---|---|---|
| 7,257,438 B2 | 8/2007 | Kinast |
| 7,277,752 B2 | 10/2007 | Matos |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,116,841 B2 | 2/2012 | Bly et al. |
| 8,150,502 B2 | 4/2012 | Kumar et al. |
| 8,160,682 B2 | 4/2012 | Kumar et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 * | 8/2012 | Felix ............ A61B 5/0404 600/509 |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,554,311 B2 | 10/2013 | Warner et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,903,484 B2 | 12/2014 | Mazar |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,277,864 B2 | 3/2016 | Yang et al. |
| 9,339,202 B2 | 5/2016 | Brockway et al. |
| 9,439,566 B2 | 9/2016 | Arne et al. |
| 9,737,211 B2 * | 8/2017 | Bardy ............... A61B 5/0006 |
| 2002/0013538 A1 | 1/2002 | Teller |
| 2002/0013717 A1 | 1/2002 | Ando et al. |
| 2002/0103422 A1 | 8/2002 | Harder et al. |
| 2002/0120310 A1 | 8/2002 | Linden et al. |
| 2002/0184055 A1 | 12/2002 | Naghavi et al. |
| 2002/0193668 A1 * | 12/2002 | Munneke ........ A61B 5/04325 600/300 |
| 2003/0004547 A1 | 1/2003 | Owen et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0148194 A1 | 7/2004 | Wellons et al. |
| 2004/0207530 A1 | 10/2004 | Nielsen |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0096717 A1 | 5/2005 | Bishay et al. |
| 2005/0108055 A1 | 5/2005 | Ott et al. |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0041201 A1 | 2/2006 | Behbehani et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0051668 A1 | 2/2008 | Bardy |
| 2008/0058661 A1 | 3/2008 | Bardy |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |

(56) References Cited

U.S. PATENT DOCUMENTS

| | | |
|---|---|---|
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0306359 A1 | 12/2008 | Zdeblick et al. |
| 2008/0312522 A1 | 12/2008 | Rowlandson |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0234715 A1 | 9/2010 | Shin et al. |
| 2010/0234716 A1 | 9/2010 | Engel |
| 2010/0280366 A1 | 11/2010 | Arne et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0066041 A1 | 3/2011 | Pandia et al. |
| 2011/0077497 A1 | 3/2011 | Oster et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russell et al. |
| 2012/0306662 A1 | 6/2012 | Vosch et al. |
| 2012/0172695 A1 | 7/2012 | Ko et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0225963 A1 | 8/2013 | Kodandaramaiah et al. |
| 2013/0225966 A1 | 8/2013 | Barber et al. |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Barber et al. |
| 2014/0056452 A1 | 2/2014 | Moss et al. |
| 2014/0140359 A1 | 5/2014 | Kalevo et al. |
| 2014/0189928 A1 | 7/2014 | Oleson et al. |
| 2014/0206977 A1 | 7/2014 | Bahney et al. |
| 2014/0215246 A1 | 7/2014 | Lee et al. |
| 2014/0358193 A1 | 12/2014 | Lyons et al. |
| 2015/0048836 A1 | 2/2015 | Guthrie et al. |
| 2015/0065842 A1 | 3/2015 | Lee et al. |
| 2015/0177175 A1 | 6/2015 | Elder et al. |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0217691 A1 | 7/2016 | Kadobayashi et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | 2004129788 | 4/2004 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |

OTHER PUBLICATIONS

Alivecor, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants At Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

(56) References Cited

OTHER PUBLICATIONS

Smith, Jawbone Up, URL <http://www.businessinsider.com/fitbit-flex-vs-jawbone-up-2013-5?op=1> (Jun. 1, 2013).
Kligfield, Paul et al., Recommendations for the Standardization and Interpretation of the Electrocardiogram: Part I. J.Am.Coll. Cardiol; 2007; 49; 1109-27, 75 Pgs.
Lauren Gravitz, "When Your Diet Needs a Band-Aid," Technology Review, MIT. (May 1, 2009).
Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4751.
McManus et al., "A Novel Application for the Detection of an Irregular Pulse using an iPhone 4S in Patients with Atrial Fibrillation," vol. 10(3), pp. 315-319 (Mar. 2013.).
Nike+ Fuel Band, URL <http://www.nike.com/us/en_us/c/nikeplus-fuelband> (Web page cached on Jan. 11, 2013.).
P. Libby et al.,"Braunwald's Heart Disease—A Textbook of Cardiovascular Medicine," Chs. 11, pp. 125-148 and 12, pp. 149-193 (8th ed. 2008), American Heart Association.
Polar Loop, URL <http://www.dcrainmaker.com/2013/09/polar-loop-firstlook.html>.
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2013.).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2013).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S." Endurance Sportswire—Endurance Sportswire. Jul. 11, 2013 URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
https://web.archive.org/web/20130831204020/http://www.biopac.com/research.asp?CatID=37&Main=Software (Aug. 2013).
Adinstruments:ECG Analysis Module for LabChart & PowerLab, 2008.
BIOPAC Systems, Inc. #AS148-Automated ECG Analysis , Mar. 24, 2006.

\* cited by examiner

ECG Datastream Symbol Encoding

| (ECG[n] – Accumulated Value) | | Code/Encoding |
|---|---|---|
| Min | Max | |
| -10 | +10 | 0 |
| +11 | +20 | 1 |
| +21 | +40 | 2 |
| +41 | +150 | 3 |
| +151 | +300 | 4 |
| +301 | +1500 | 5 |
| +1501 | +5000 | 6 |
| +5001 | +50,000 | 7 |
| -11 | -20 | -1 |
| -21 | -40 | -2 |
| -41 | -150 | -3 |
| -151 | -300 | -4 |
| -301 | -1500 | -5 |
| -1501 | -5000 | -6 |
| -5001 | -50,000 | -7 |

Example:

| n | ECG[n] | Accumulator | ECG[n]-Accumulator | Encoding | Delta | Decoding |
|---|--------|-------------|--------------------|----------|-------|----------|
| 0 | 12000  | 12000       | 0                  | 0        | 0     | 12000    |
| 1 | 11904  | 12000       | -96                | -3       | -41   | 11959    |
| 2 | 12537  | 11959       | 578                | +5       | +301  | 12260    |

Fig. 27. (Con'd).
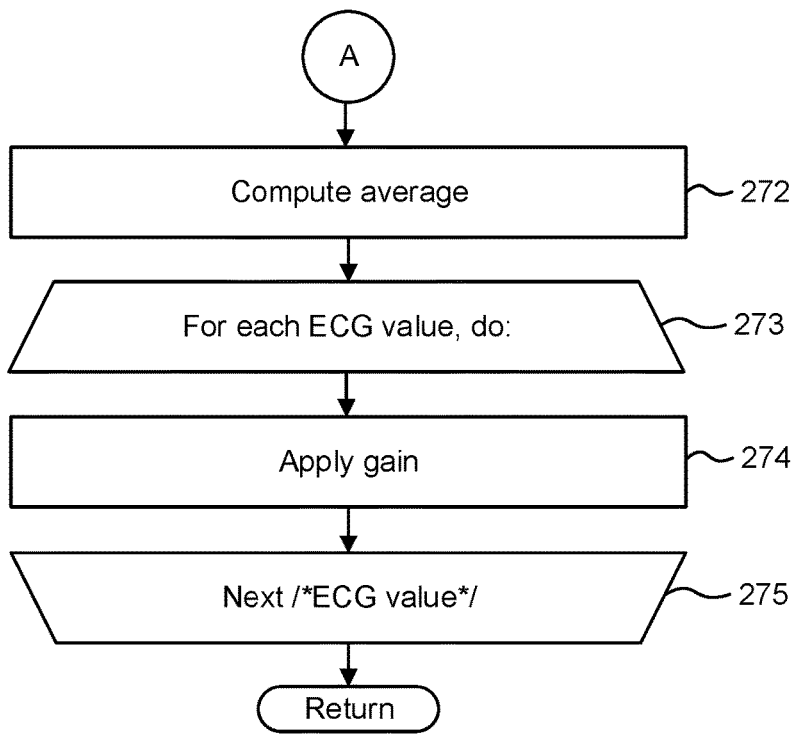
Fig. 28.
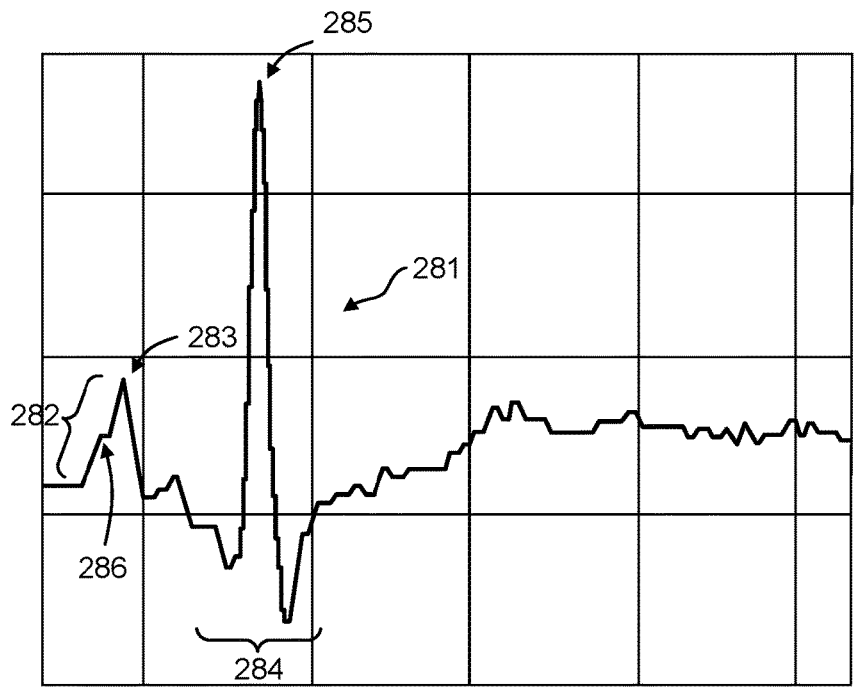

SYSTEM AND METHOD FOR PROVIDING DYNAMIC GAIN OVER NON-NOISE ELECTROCARDIOGRAPHIC DATA WITH THE AID OF A DIGITAL COMPUTER

CROSS-REFERENCE TO RELATED APPLICATION

This non-provisional patent application is a continuation of U.S. Pat. No. 9,737,211, issued Aug. 22, 2017, which is a continuation of U.S. Pat. No. 9,554,715, issued Jan. 31, 2017, which is a continuation of U.S. Pat. No. 9,345,414, issued May 24, 2016, which is a continuation-in-part of U.S. Pat. No. 9,408,545, issued Aug. 9, 2016, which is a continuation-in-part of U.S. Pat. No. 9,700,227, issued Jul. 11, 2017, which is a continuation-in-part of U.S. Pat. No. 9,730,593, issued Aug. 15, 2017, and further claims priority under 35 U.S.C. § 119(e) to U.S. Provisional Patent application, Ser. No. 61/882,403, filed Sep. 25, 2013, the disclosures of which are incorporated by reference.

FIELD

This application relates in general to electrocardiographic monitoring and, in particular, to a system and method for providing dynamic gain over non-noise electrocardiographic data with the aid of a digital computer.

BACKGROUND

The first electrocardiogram (ECG) was invented by a Dutch physiologist, Willem Einthoven, in 1903, who used a string galvanometer to measure the electrical activity of the heart. Generations of physicians around the world have since used ECGs, in various forms, to diagnose heart problems and other potential medical concerns. Although the basic principles underlying Dr. Einthoven's original work, including his naming of various waveform deflections (Einthoven's triangle), are still applicable today, ECG machines have evolved from his original three-lead ECG, to ECGs with unipolar leads connected to a central reference terminal starting in 1934, to augmented unipolar leads beginning in 1942, and finally to the 12-lead ECG standardized by the American Heart Association in 1954 and still in use today. Further advances in portability and computerized interpretation have been made, yet the electronic design of the ECG recording apparatuses has remained fundamentally the same for much of the past 40 years.

An ECG measures the electrical signals emitted by the heart as generated by the propagation of the action potentials that trigger depolarization of heart fibers. Physiologically, transmembrane ionic currents are generated within the heart during cardiac activation and recovery sequences. Cardiac depolarization originates high in the right atrium in the sinoatrial (SA) node before spreading leftward towards the left atrium and inferiorly towards the atrioventricular (AV) node. After a delay occasioned by the AV node, the depolarization impulse transits the Bundle of His and moves into the right and left bundle branches and Purkinje fibers to activate the right and left ventricles.

During each cardiac cycle, the ionic currents create an electrical field in and around the heart that can be detected by ECG electrodes placed on the skin. Cardiac electrical activity can then be visually represented in an ECG trace in PQRSTU-waveforms. The P-wave represents atrial electrical activity, and the QRSTU components represent ventricular electrical activity. Specifically, a P-wave represents atrial depolarization, which causes atrial contraction.

P-wave analysis based on ECG monitoring is critical to accurate cardiac rhythm diagnosis and focuses on localizing the sites of origin and pathways of arrhythmic conditions. P-wave analysis is also used in the diagnosis of other medical disorders, including blood chemistry imbalance. Cardiac arrhythmias are defined by the morphology of P-waves and their relationship to QRS intervals. For instance, atrial fibrillation (AF), an abnormally rapid heart rhythm, can be confirmed by an absence of P-waves and an irregular ventricular rate. Similarly, sinoatrial block can be characterized by a delay in the onset of P-waves, while junctional rhythm, an abnormal heart rhythm resulting from impulses coming from a locus of tissue in the area of the AV node, usually presents without P-waves or with inverted P-waves. The amplitudes of P-waves are also valuable for diagnosis. The presence of broad, notched P-waves can indicate left atrial enlargement. Conversely, the presence of tall, peaked P-waves can indicate right atrial enlargement. Finally, P-waves with increased amplitude can indicate hypokalemia, caused by low blood potassium, whereas P-waves with decreased amplitude can indicate hyperkalemia, caused by elevated blood potassium.

Cardiac rhythm disorders may present with lightheadedness, fainting, chest pain, hypoxia, syncope, palpitations, and congestive heart failure (CHF), yet rhythm disorders are often sporadic in occurrence and may not show up in-clinic during a conventional 12-second ECG. Continuous ECG monitoring with P-wave-centric action potential acquisition over an extended period is more apt to capture sporadic cardiac events. However, recording sufficient ECG and related physiological data over an extended period remains a significant challenge, despite an over 40-year history of ambulatory ECG monitoring efforts combined with no appreciable improvement in P-wave acquisition techniques since Dr. Einthoven's original pioneering work over a 110 years ago.

Electrocardiographic monitoring over an extended period provides a physician with the kinds of data essential to identifying the underlying cause of sporadic cardiac conditions, especially rhythm disorders, and other physiological events of potential concern. A 30-day observation period is considered the "gold standard" of monitoring, yet a 14-day observation period is currently pitched as being achievable by conventional ECG monitoring approaches. Realizing a 30-day observation period has proven unworkable with existing ECG monitoring systems, which are arduous to employ; cumbersome, uncomfortable and not user-friendly to the patient; and costly to manufacture and deploy. Still, if a patient's ECG could be recorded in an ambulatory setting over a prolonged time periods, particularly for more than 14 days, thereby allowing the patient to engage in activities of daily living, the chances of acquiring meaningful medical information and capturing an abnormal event while the patient is engaged in normal activities are greatly improved.

The location of the atria and their low amplitude, low frequency content electrical signals make P-waves difficult to sense, particularly through ambulatory ECG monitoring. The atria are located posteriorly within the chest, and their physical distance from the skin surface adversely affects current strength and signal fidelity. Cardiac electrical potentials measured dermally have an amplitude of only one-percent of the amplitude of transmembrane electrical potentials. The distance between the heart and ECG electrodes reduces the magnitude of electrical potentials in proportion to the square of change in distance, which compounds the problem of sensing low amplitude P-waves. Moreover, the tissues and structures that lie between the activation regions within the heart and the body's surface alter the cardiac electrical field due to changes in the electrical resistivity of adjacent tissues. Thus, surface electrical potentials, when even capable of being accurately detected, are smoothed over in aspect and bear only a general spatial relationship to actual underlying cardiac events, thereby complicating diagnosis. Conventional 12-lead ECGs attempt to compensate for weak P-wave signals by monitoring the heart from multiple perspectives and angles, while conventional ambulatory ECGs primarily focus on monitoring higher amplitude ventricular activity that can be readily sensed. Both approaches are unsatisfactory with respect to the P-wave and the accurate, medically actionable diagnosis of the myriad cardiac rhythm disorders that exist.

Additionally, maintaining continual contact between ECG electrodes and the skin after a day or two of ambulatory ECG monitoring has been a problem. Time, dirt, moisture, and other environmental contaminants, as well as perspiration, skin oil, and dead skin cells from the patient's body, can get between an ECG electrode's non-conductive adhesive and the skin's surface. These factors adversely affect electrode adhesion and the quality of cardiac signal recordings. Furthermore, the physical movements of the patient and their clothing impart various compressional, tensile, bending, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, multi-week or multi-month monitoring can be performed by implantable ECG monitors, such as the Reveal LINQ insertable cardiac monitor, manufactured by Medtronic, Inc., Minneapolis, Minn. This monitor can detect and record paroxysmal or asymptomatic arrhythmias for up to three years. However, like all forms of implantable medical device (IMD), use of this monitor requires invasive surgical implantation, which significantly increases costs; requires ongoing follow up by a physician throughout the period of implantation; requires specialized equipment to retrieve monitoring data; and carries complications attendant to all surgery, including risks of infection, injury or death.

Holter monitors are widely used for extended ECG monitoring. Typically, they are often used for only 24-48 hours. A typical Holter monitor is a wearable and portable version of an ECG that include cables for each electrode placed on the skin and a separate battery-powered ECG recorder. The leads are placed in the anterior thoracic region in a manner similar to what is done with an in-clinic standard ECG machine using electrode locations that are not specifically intended for optimal P-wave capture. The duration of monitoring depends on the sensing and storage capabilities of the monitor. A "looping" Holter (or event) monitor can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest precludes a patient from replacing or removing the sensing leads and usually involves moving the patient from the physician office to a specialized center within the hospital or clinic.

U.S. Pat. No. 8,460,189, to Libbus et al. ("Libbus") discloses an adherent wearable cardiac monitor that includes at least two measurement electrodes and an accelerometer. The device includes a reusable electronics module and a disposable adherent patch that includes the electrodes. ECG monitoring can be conducted using multiple disposable patches adhered to different locations on the patient's body. The device includes a processor configured to control collection and transmission of data from ECG circuitry, including generating and processing of ECG signals and data acquired from two or more electrodes. The ECG circuitry can be coupled to the electrodes in many ways to define an ECG vector, and the orientation of the ECG vector can be determined in response to the polarity of the measurement electrodes and orientation of the electrode measurement axis. The accelerometer can be used to determine the orientation of the measurement electrodes in each of the locations. The ECG signals measured at different locations can be rotated based on the accelerometer data to modify amplitude and direction of the ECG features to approximate a standard ECG vector. The signals recorded at different locations can be combined by summing a scaled version of each signal. Libbus further discloses that inner ECG electrodes may be positioned near outer electrodes to increase the voltage of measured ECG signals. However, Libbus treats ECG signal acquisition as the measurement of a simple aggregate directional data signal without differentiating between the distinct kinds of cardiac electrical activities presented with an ECG waveform, particularly atrial (P-wave) activity.

The ZIO XT Patch and ZIO Event Card devices, manufactured by iRhythm Tech., Inc., San Francisco, Calif., are wearable monitoring devices that are typically worn on the upper left pectoral region to respectively provide continuous and looping ECG recording. The location is used to simulate surgically implanted monitors, but without specifically enhancing P-wave capture. Both of these devices are prescription-only and for single patient use. The ZIO XT Patch device is limited to a 14-day period, while the electrodes only of the ZIO Event Card device can be worn for up to 30 days. The ZIO XT Patch device combines both electronic recordation components and physical electrodes into a unitary assembly that adheres to the patient's skin. The ZIO XT Patch device uses adhesive sufficiently strong to support the weight of both the monitor and the electrodes over an extended period and to resist disadherence from the patient's body, albeit at the cost of disallowing removal or relocation during the monitoring period. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of cardiac electrical potential signals, especially atrial (P-wave) signals.

ECG signals contain a large amount of information that requires large storage space, large transmission bandwidth, and long transmission time. Long-term ECG monitoring further increases the amount of information to be stored and processed. Data compression is useful in ECG applications, especially long-term monitoring. Data compression can reduce the requirement for data storage space, reduce power consumption, and extends monitoring time. ECG compression can be evaluated based on compression ratio, signal error loss, and time of execution. A good ECG data compression preferably should preserve the useful diagnostic information while compressing a signal to a smaller acceptable size. Currently, many Holter monitors use some types of compression algorithm; however, compression ratios are not satisfactory.

Therefore, a need remains for a low cost extended wear continuously recording ECG monitor that is low power and storage space and data transmission efficient, therefore contributing to long-term use.

SUMMARY

Physiological monitoring can be provided through a lightweight wearable monitor that includes two components, a flexible extended wear electrode patch and a reusable monitor recorder that removably snaps into a receptacle on the electrode patch. The wearable monitor sits centrally (in the midline) on the patient's chest along the sternum oriented top-to-bottom. The ECG electrodes on the electrode patch are tailored to be positioned axially along the midline of the sternum for capturing action potential propagation in an orientation that corresponds to the aVF lead used in a conventional 12-lead ECG that is used to sense positive or upright P-waves. The placement of the wearable monitor in a location at the sternal midline (or immediately to either side of the sternum), with its unique narrow "hourglass"-like shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms.

Moreover, the electrocardiography monitor offers superior patient comfort, convenience and user-friendliness. The electrode patch is specifically designed for ease of use by a patient (or caregiver); assistance by professional medical personnel is not required. The patient is free to replace the electrode patch at any time and need not wait for a doctor's appointment to have a new electrode patch placed. Patients can easily be taught to find the familiar physical landmarks on the body necessary for proper placement of the electrode patch. Empowering patients with the knowledge to place the electrode patch in the right place ensures that the ECG electrodes will be correctly positioned on the skin, no matter the number of times that the electrode patch is replaced. In addition, the monitor recorder operates automatically and the patient only need snap the monitor recorder into place on the electrode patch to initiate ECG monitoring. Thus, the synergistic combination of the electrode patch and monitor recorder makes the use of the electrocardiography monitor a reliable and virtually foolproof way to monitor a patient's ECG and physiology for an extended, or even open-ended, period of time.

Furthermore, the ECG data collected during the long-term monitoring are compressed through a two-step compression algorithm executed by the electrocardiography monitor. Minimum amplitude signals may be masked by or become indistinguishable from noise if overly inclusive encoding is employed in which voltage ranges are set too wide. The resulting ECG signal will appear "choppy" and uneven with an abrupt (and physiologically inaccurate and potentially misleading) slope. Thus, the encoding used in the first stage of compression can be dynamically rescaled on-the-fly when the granularity of the encoding is too coarse.

Finally, offloaded ECG signals are automatically gained as appropriate on a recording-by-recording basis to preserve the amplitude relationship between the signals. Raw decompressed ECG signals are filtered for noise content and any gaps in the signals are bridged. The signal is then gained based on a statistical evaluation of peak-to-peak voltage (or other indicator) to land as many ECG waveforms within a desired range of display.

In one embodiment, a system and method for providing dynamic gain over non-noise electrocardiographic data with the aid of a digital computer are provided. A time series of a plurality of voltage values that comprises a digital representation of a raw electrocardiography ("ECG") signal recorded by an ambulatory monitor recorder is obtained. One or more segments of the ECG signal is marked as noise, each of the segments including a plurality of the values, based on a difference between a maximum one and a minimum one of the values within that segment. Further segments not marked as noise are analyzed, each of the segments comprising a plurality of the values. A gain factor for all of the values in the analyzed further segments is determined based on the analysis.

In a further embodiment, an ambulatory adjustable encoding monitor recorder is provided. The monitor recorder includes a memory configured to store a plurality of codes and a plurality of electrocardiographic values associated with each of the codes and a microcontroller configured to sense electrocardiographic values during a sequence of temporal windows and to process the electrocardiographic values within each of the windows, the processing including: calculate a mathematical relationship between a maximum one and a minimum one of the electrocardiographic values in each of the temporal windows; compare each of the relationship to an at least one threshold; based on the comparison of the relationship for at least one of the windows, adjust the plurality of the electrocardiographic values associated with each of the codes; encode each of the electrocardiography values within that window with one of the codes based on the adjusted plurality of the electrocardiographic values associated with that code; and write each of the codes into a sequence in the memory of the monitor recorder.

The foregoing aspects enhance ECG monitoring performance and quality by facilitating long-term ECG recording, which is critical to accurate arrhythmia and cardiac rhythm disorder diagnoses.

The monitoring patch is especially suited to the female anatomy, although also easily used over the male sternum. The narrow longitudinal midsection can fit nicely within the inter-mammary cleft of the breasts without inducing discomfort, whereas conventional patch electrodes are wide and, if adhered between the breasts, would cause chafing, irritation, discomfort, and annoyance, leading to low patient compliance.

In addition, the foregoing aspects enhance comfort in women (and certain men), but not irritation of the breasts, by placing the monitoring patch in the best location possible for optimizing the recording of cardiac signals from the atrium, particularly P-waves, which is another feature critical to proper arrhythmia and cardiac rhythm disorder diagnoses.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 24 is an example of a panel of codes or encodings with each code covering a range defined by a lower threshold ECG value and an upper threshold ECG value.

FIG. 25 is an illustrating the encoding and compression scheme in accordance with method and parameters as described with reference to in FIGS. 23 and 24.

FIG. 28 is a graph showing, by way of example, an ECG waveform with a low amplitude signal that has been degraded by compression artifacts.

DETAILED DESCRIPTION

Figure 1:
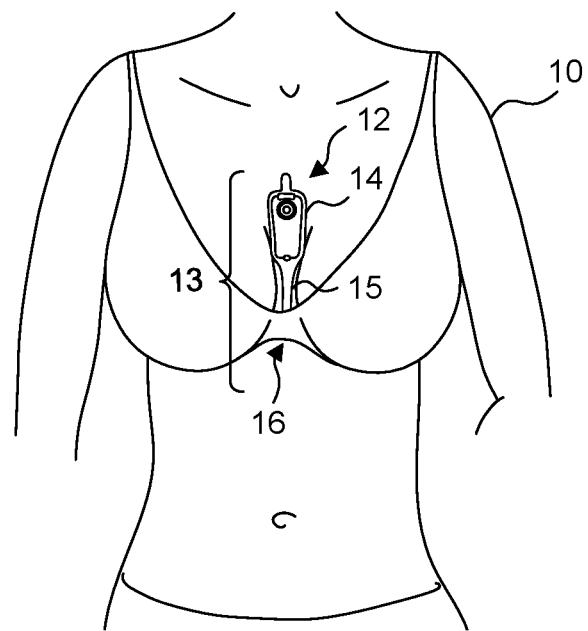
FIGS. 1 and 2 are diagrams showing, by way of examples, an extended wear electrocardiography monitor, including an extended wear electrode patch, in accordance with one embodiment, respectively fitted to the sternal region of a female patient and a male patient.
Figure 2:
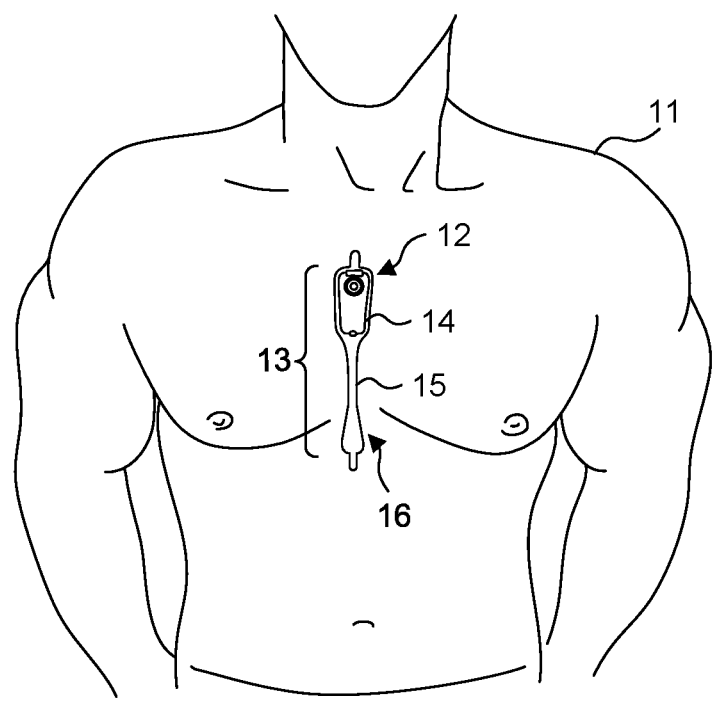

ECG and physiological monitoring can be provided through a wearable ambulatory monitor that includes two components, a flexible extended wear electrode patch and a removable reusable (or single use) monitor recorder. Both the electrode patch and the monitor recorder are optimized to capture electrical signals from the propagation of low amplitude, relatively low frequency content cardiac action potentials, particularly the P-waves generated during atrial activation. FIGS. 1 and 2 are diagrams showing, by way of examples, an extended wear electrocardiography monitor 12, including a monitor recorder 14, in accordance with one embodiment, respectively fitted to the sternal region of a female patient 10 and a male patient 11. The wearable monitor 12 sits centrally, positioned axially along the sternal midline 16, on the patient's chest along the sternum 13 and oriented top-to-bottom with the monitor recorder 14 preferably situated towards the patient's head. In a further embodiment, the orientation of the wearable monitor 12 can be corrected post-monitoring, as further described infra, for instance, if the wearable monitor 12 is inadvertently fitted upside down.

The electrode patch 15 is shaped to fit comfortably and conformal to the contours of the patient's chest approximately centered on the sternal midline 16 (or immediately to either side of the sternum 13). The distal end of the electrode patch 15, under which a lower or inferior pole (ECG electrode) is adhered, extends towards the Xiphoid process and lower sternum and, depending upon the patient's build, may straddle the region over the Xiphoid process and lower sternum. The proximal end of the electrode patch 15, located under the monitor recorder 14, under which an upper or superior pole (ECG electrode) is adhered, is below the manubrium and, depending upon patient's build, may straddle the region over the manubrium.

During ECG monitoring, the amplitude and strength of action potentials sensed on the body's surface are affected to varying degrees by cardiac, cellular, extracellular, vector of current flow, and physical factors, like obesity, dermatitis, large breasts, and high impedance skin, as can occur in dark-skinned individuals. Sensing along the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity by countering some of the effects of these factors.

Figure 3:
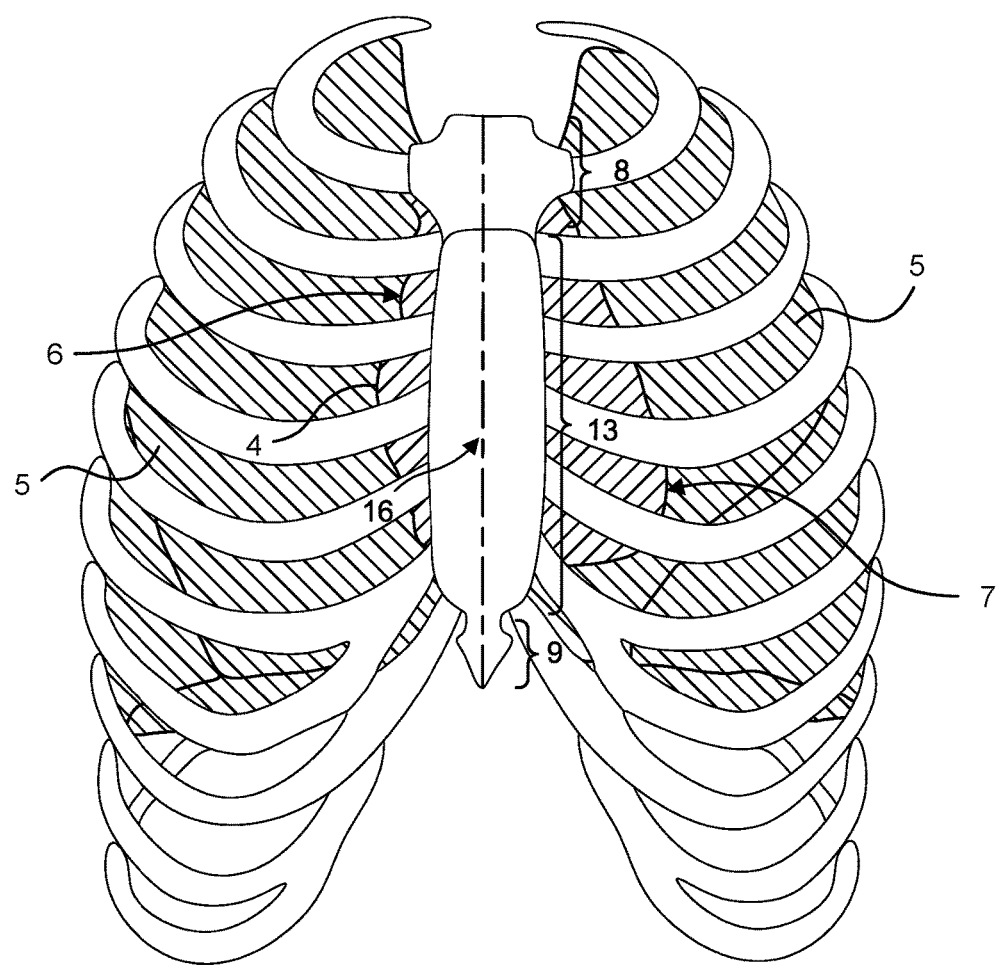
FIG. 3 is a front anatomical view showing, by way of illustration, the locations of the heart and lungs within the rib cage of an adult human.

The ability to sense low amplitude, low frequency content body surface potentials is directly related to the location of ECG electrodes on the skin's surface and the ability of the sensing circuitry to capture these electrical signals. FIG. 3 is a front anatomical view showing, by way of illustration, the locations of the heart 4 and lungs 5 within the rib cage of an adult human. Depending upon their placement locations on the chest, ECG electrodes may be separated from activation regions within the heart 4 by differing combinations of internal tissues and body structures, including heart muscle, intracardiac blood, the pericardium, intrathoracic blood and fluids, the lungs 5, skeletal muscle, bone structure, subcutaneous fat, and the skin, plus any contaminants present between the skin's surface and electrode signal pickups. The degree of amplitude degradation of cardiac transmembrane potentials increases with the number of tissue boundaries between the heart 4 and the skin's surface that are encountered. The cardiac electrical field is degraded each time the transmembrane potentials encounter a physical boundary separating adjoining tissues due to differences in the respective tissues' electrical resistances. In addition, other non-spatial factors, such as pericardial effusion, emphysema or fluid accumulation in the lungs, as further explained infra, can further degrade body surface potentials.

Internal tissues and body structures can adversely affect the current strength and signal fidelity of all body surface potentials, yet low amplitude cardiac action potentials, particularly the P-wave with a normative amplitude of less than 0.25 microvolts (mV) and a normative duration of less than 120 milliseconds (ms), are most apt to be negatively impacted. The atria 6 are generally located posteriorly within the thoracic cavity (with the exception of the anterior right atrium and right atrial appendage), and, physically, the left atrium constitutes the portion of the heart 4 furthest away from the surface of the skin on the chest. Conversely, the ventricles 7, which generate larger amplitude signals, generally are located anteriorly with the anterior right ventricle and most of the left ventricle situated relatively close to the skin surface on the chest, which contributes to the relatively stronger amplitudes of ventricular waveforms. Thus, the quality of P-waves (and other already-low amplitude action potential signals) is more susceptible to weakening from intervening tissues and structures than the waveforms associated with ventricular activation.

The importance of the positioning of ECG electrodes along the sternal midline 15 has largely been overlooked by conventional approaches to ECG monitoring, in part due to the inability of their sensing circuitry to reliably detect low amplitude, low frequency content electrical signals, particularly in P-waves. In turn, that inability to keenly sense P-waves has motivated ECG electrode placement in other non-sternal midline thoracic locations, where the QRSTU components that represent ventricular electrical activity are more readily detectable by their sensing circuitry than P-waves. In addition, ECG electrode placement along the sternal midline 15 presents major patient wearability challenges, such as fitting a monitoring ensemble within the narrow confines of the inter-mammary cleft between the breasts, that to large extent drive physical packaging concerns, which can be incompatible with ECG monitors intended for placement, say, in the upper pectoral region or other non-sternal midline thoracic locations. In contrast, the wearable monitor 12 uses an electrode patch 15 that is specifically intended for extended wear placement in a location at the sternal midline 16 (or immediately to either side of the sternum 13). When combined with a monitor recorder 14 that uses sensing circuitry optimized to preserve the characteristics of low amplitude cardiac action potentials, especially those signals from the atria, as further described infra with reference to FIG. 11, the electrode patch 15 helps to significantly improve atrial activation (P-wave) sensing through placement in a body location that robustly minimizes the effects of tissue and body structure.

Referring back to FIGS. 1 and 2, the placement of the wearable monitor 12 in the region of the sternal midline 13 puts the ECG electrodes of the electrode patch 15 in locations better adapted to sensing and recording low amplitude cardiac action potentials during atrial propagation (P-wave signals) than placement in other locations, such as the upper left pectoral region, as commonly seen in most conventional ambulatory ECG monitors. The sternum 13 overlies the right atrium of the heart 4. As a result, action potential signals have to travel through fewer layers of tissue and structure to reach the ECG electrodes of the electrode patch 15 on the body's surface along the sternal midline 13 when compared to other monitoring locations, a distinction that is of critical importance when capturing low frequency content electrical signals, such as P-waves.

Moreover, cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the AV node. The ECG electrodes of the electrode patch 15 are placed with the upper or superior pole (ECG electrode) along the sternal midline 13 in the region of the manubrium and the lower or inferior pole (ECG electrode) along the sternal midline 13 in the region of the Xiphoid process 9 and lower sternum. The ECG electrodes are placed primarily in a north-to-south orientation along the sternum 13 that corresponds to the north-to-south waveform vector exhibited during atrial activation. This orientation corresponds to the aVF lead used in a conventional 12-lead ECG that is used to sense positive or upright P-waves.

Furthermore, the thoracic region underlying the sternum 13 along the midline 16 between the manubrium 8 and Xiphoid process 9 is relatively free of lung tissue, musculature, and other internal body structures that could occlude the electrical signal path between the heart 4, particularly the atria, and ECG electrodes placed on the surface of the skin. Fewer obstructions means that cardiac electrical potentials encounter fewer boundaries between different tissues. As a result, when compared to other thoracic ECG sensing locations, the cardiac electrical field is less altered when sensed dermally along the sternal midline 13. As well, the proximity of the sternal midline 16 to the ventricles 7 facilitates sensing of right ventricular activity and provides superior recordation of the QRS interval, again, in part due to the relatively clear electrical path between the heart 4 and the skin surface.

Finally, non-spatial factors can affect transmembrane action potential shape and conductivity. For instance, myocardial ischemia, an acute cardiac condition, can cause a transient increase in blood perfusion in the lungs 5. The perfused blood can significantly increase electrical resistance across the lungs 5 and therefore degrade transmission of the cardiac electrical field to the skin's surface. However, the placement of the wearable monitor 12 along the sternal midline 16 in the inter-mammary cleft between the breasts is relatively resilient to the adverse effects to cardiac action potential degradation caused by ischemic conditions as the body surface potentials from a location relatively clear of underlying lung tissue and fat help compensate for the loss of signal amplitude and content. The monitor recorder 14 is thus able to record the P-wave morphology that may be compromised by myocardial ischemia and therefore make diagnosis of the specific arrhythmias that can be associated with myocardial ischemia more difficult.

Figure 4:
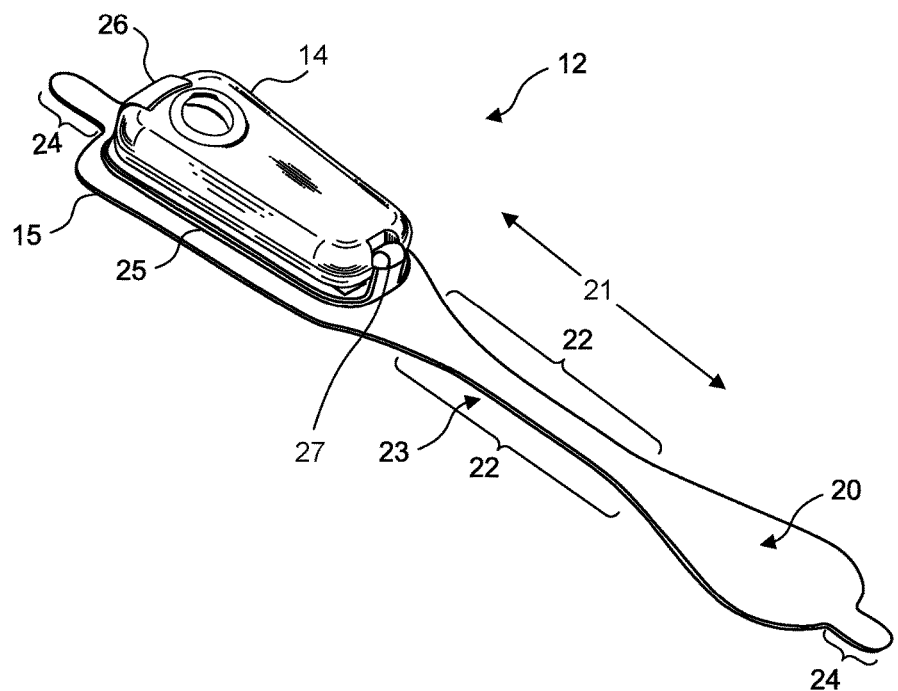
FIG. 4 is a perspective view showing an extended wear electrode patch in accordance with one embodiment with a monitor recorder inserted.

During use, the electrode patch 15 is first adhered to the skin along the sternal midline 16 (or immediately to either side of the sternum 13). A monitor recorder 14 is then snapped into place on the electrode patch 15 using an electro mechanical docking interface to initiate ECG monitoring. FIG. 4 is a perspective view showing an extended wear electrode patch 15 in accordance with one embodiment with a monitor recorder 14 inserted. The body of the electrode patch 15 is preferably constructed using a flexible backing 20 formed as an elongated strip 21 of wrap knit or similar stretchable material about 145 mm long and 32 mm at the widest point with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above, such as described in commonly-assigned U.S. Design Pat. No. D744,659, issued Dec. 1, 2015, the disclosure of which is incorporated by reference. The upper part of the "hourglass" is sized to allow an electrically non-conductive receptacle 25, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile (but still rounded and tapered to fit comfortably between the breasts) than the lower part of the "hourglass," which is sized primarily to allow just the placement of an ECG electrode of appropriate shape and surface area to record the P-wave and the QRS signals sufficiently given the inter-electrode spacing.

The electrode patch 15 incorporates features that significantly improve wearability, performance, and patient comfort throughout an extended monitoring period. The entire electrode patch 15 is lightweight in construction, which allows the patch to be resilient to disadhesing or falling off and, critically, to avoid creating distracting discomfort to the patient, even when the patient is asleep. In contrast, the weight of a heavy ECG monitor impedes patient mobility and will cause the monitor to constantly tug downwards and press on the patient's body that can generate skin inflammation with frequent adjustments by the patient needed to maintain comfort.

During every day wear, the electrode patch 15 is subjected to pushing, pulling, and torsional movements, including compressional and torsional forces when the patient bends forward, or tensile and torsional forces when the patient leans backwards. To counter these stress forces, the electrode patch 15 incorporates crimp and strain reliefs, such as described in commonly-assigned U.S. Application Publication No. 2015/0087948, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the inter-mammary cleft between the breasts, especially in buxom women. The cut-outs 22 and narrow and flexible longitudinal midsection 23 help the electrode patch 15 fit nicely between a pair of female breasts in the inter-mammary cleft. In one embodiment, the cut-outs 22 can be graduated to form the longitudinal midsection 23 as a narrow in-between stem or isthmus portion about 7 mm wide. In a still further embodiment, tabs 24 can respectively extend an additional 8 mm to 12 mm beyond the distal and proximal ends of the flexible backing 20 to facilitate with adhering the electrode patch 15 to or removing the electrode patch 15 from the sternum 13. These tabs preferably lack adhesive on the underside, or contact, surface of the electrode patch 15. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, as further described infra beginning with reference to FIG. 9. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 30:
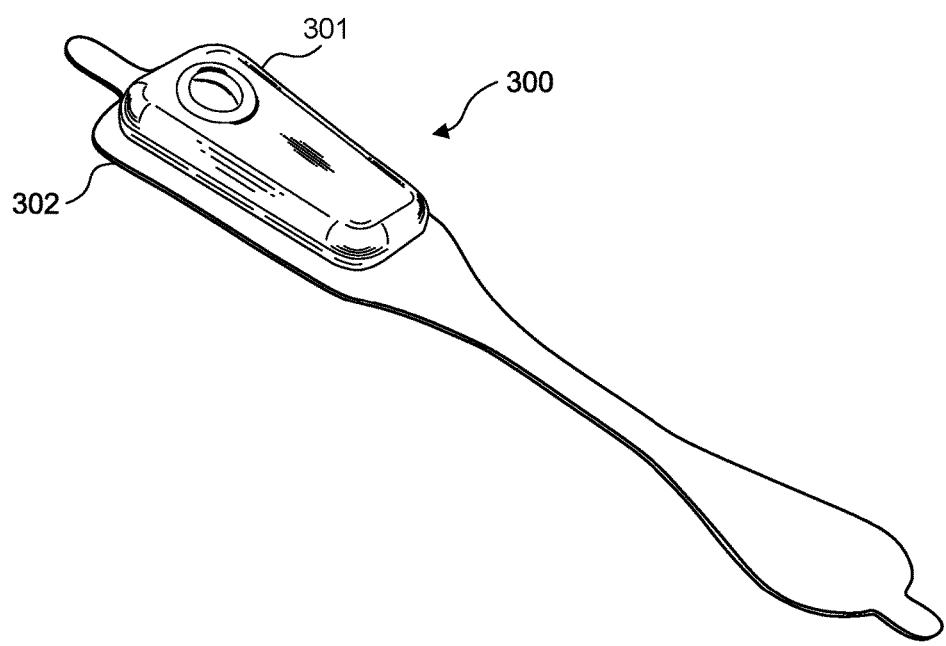
FIG. 30 is a perspective view showing a unitary extended wear electrode patch and monitor recorder assembly in accordance with a further embodiment.

The electrode patch 15 is generally intended for a single use and is meant to be replaced periodically throughout an extended period of monitoring. However, some types of monitoring may not extend over a period of time long enough to necessitate replacement of the electrode patch 15. In those situations, the monitor recorder 14 and electrode patch 15 can be combined into a single integral assembly. FIG. 30 is a perspective view showing a unitary extended wear electrode patch and monitor recorder assembly 300 in accordance with a further embodiment. The monitor recorder 301 and the electrode patch 302 are assembled as a single unit with the pair of ECG electrodes provided on the electrode patch 302 electrically connected directly into the circuitry of the monitor recorder 301, thereby obviating the need for a non-conductive receptacle or other intermediate physical coupling. The assembly 300 effectively becomes a single use type of ambulatory monitor with a usable service life dictated by the period of wear. In turn, service life can be influenced by the type of adhesive gel used to secure the electrode patch 302 to the skin and by the patient's tolerance to continued wear of the electrode patch 302 on the same spot on the skin. In a still further embodiment, the assembly 300 can be rendered reusable by either employing a form of adhesive gel that permits repeated removal and readherance of the electrode patch 302 or through replenishment of the adhesive gel. Still other forms of unitary extended wear electrode patch and monitor recorder assemblies are possible.

Figure 5:
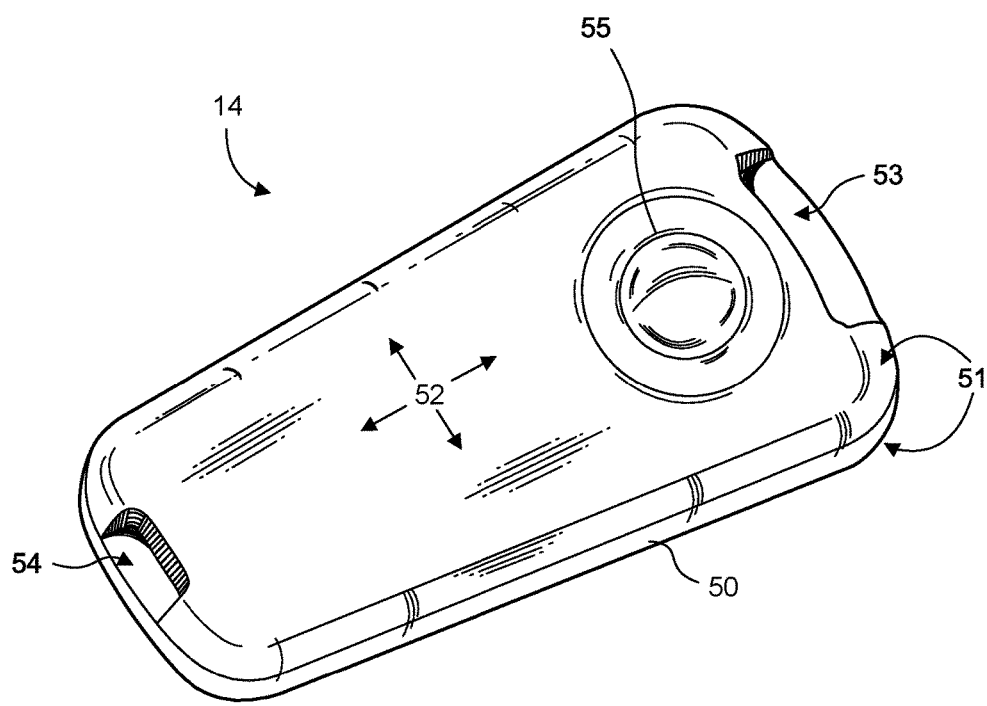
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Pat. No. D717,955, issued Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable, while the monitor recorder 14 is designed for reuse and can be transferred to successive electrode patches 15 to ensure continuity of monitoring, if so desired. The monitor recorder 14 can be used only once, but single use effectively wastes the synergistic benefits provided by the combination of the disposable electrode patch and reusable monitor recorder, as further explained infra with reference to FIGS. 16A-C. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
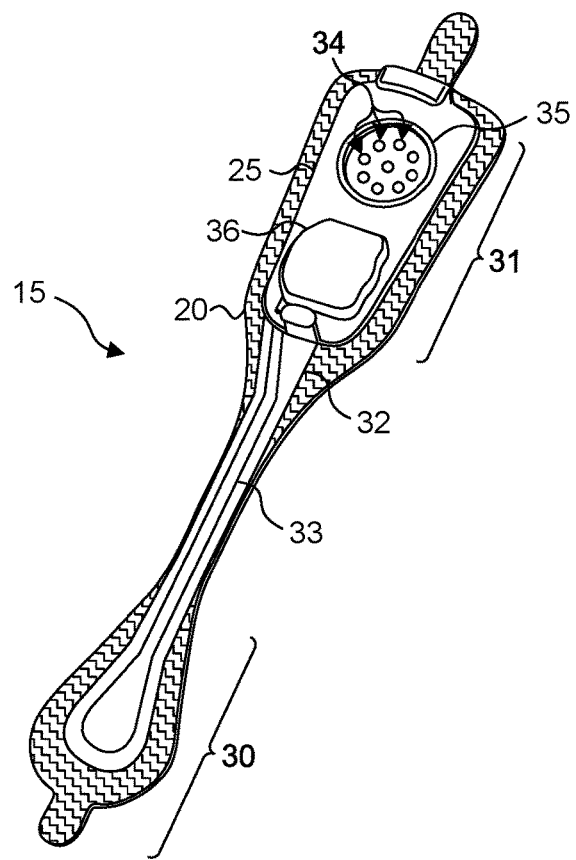
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 from the distal end 30 of the flexible backing 20 and a proximal circuit trace (not shown) from the proximal end 31 of the flexible backing 20 electrically couple ECG electrodes (not shown) with a pair of electrical pads 34. In a further embodiment, the distal and proximal circuit traces are replaced with interlaced or sewn-in flexible wires, as further described infra beginning with reference to FIG. 17. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14. The moisture-resistant seal 35 enables the monitor recorder 14 to be worn at all times, even during showering or other activities that could expose the monitor recorder 14 to moisture or adverse conditions.

In addition, a battery compartment 36 is formed on the bottom surface of the non-conductive receptacle 25. A pair of battery leads (not shown) from the battery compartment 36 to another pair of the electrical pads 34 electrically interface the battery to the monitor recorder 14. The battery contained within the battery compartment 35 is a direct current (DC) power cell and can be replaceable, rechargeable or disposable.

Figure 7:
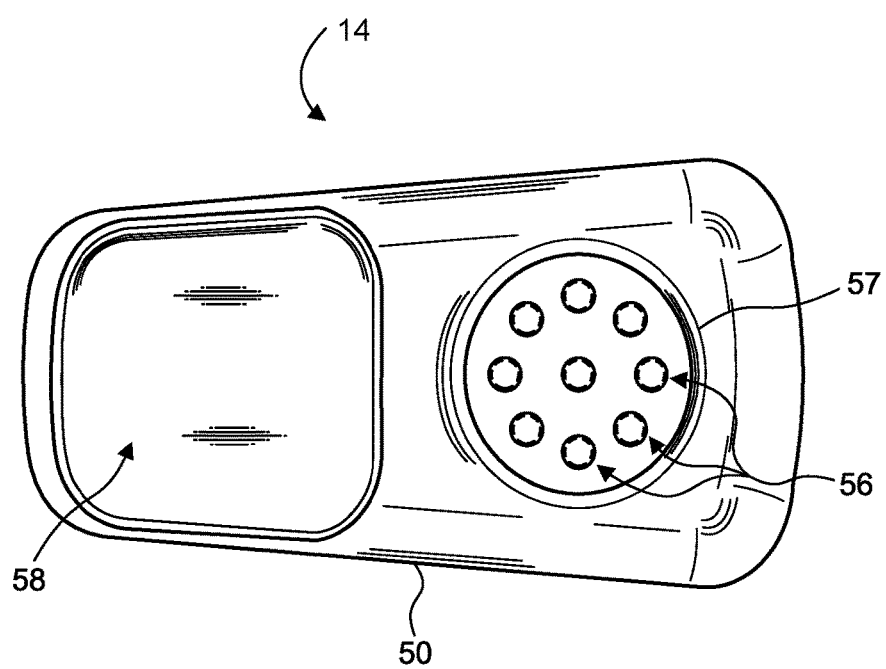
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25. The battery contained within the battery compartment 36 can be replaceable, rechargeable or disposable. In a further embodiment, the ECG sensing circuitry of the monitor recorder 14 can be supplemented with additional sensors, including an $SpO_2$ sensor, a blood pressure sensor, a temperature sensor, respiratory rate sensor, a glucose sensor, an air flow sensor, and a volumetric pressure sensor, which can be incorporated directly into the monitor recorder 14 or onto the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. However, the wearable monitor 12 is still susceptible to pushing, pulling, and torqueing movements, including compressional and torsional forces when the patient bends forward, and tensile and torsional forces when the patient leans backwards or twists. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 8:
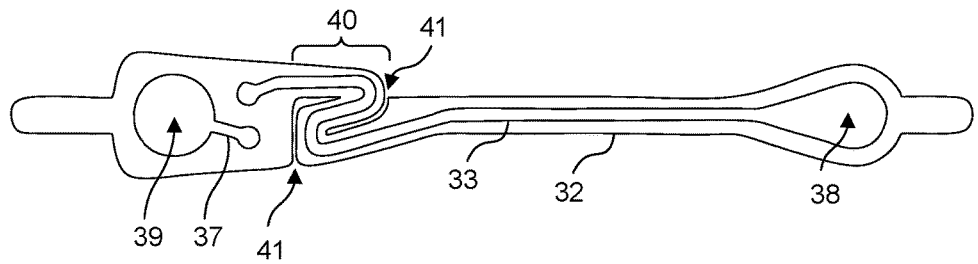
FIG. 8 is a top view showing the flexible circuit of the extended wear electrode patch of FIG. 4.

Unlike the flexible backing 20, the flexible circuit 32 is only able to bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32 to serve as electrode signal pickups. The flexible circuit 32 preferably does not extend to the outside edges of the flexible backing 20, thereby avoiding gouging or discomforting the patient's skin during extended wear, such as when sleeping on the side. During wear, the ECG electrodes 38, 39 must remain in continual contact with the skin. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to bending, tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 9:
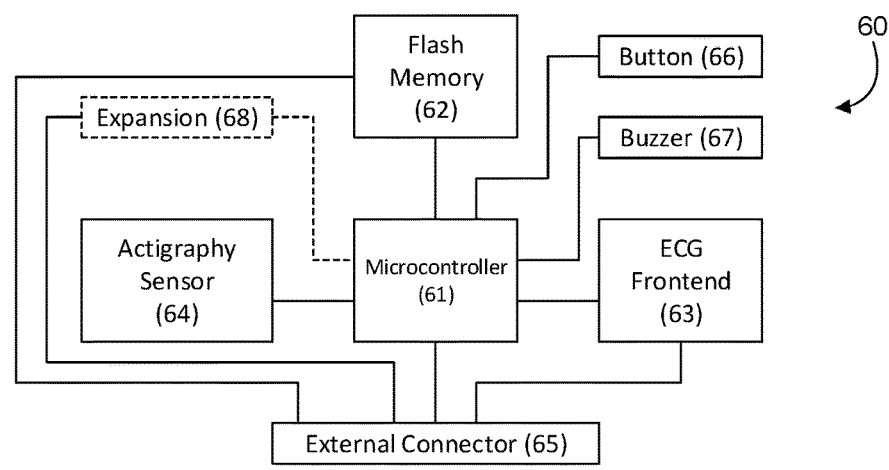
FIG. 9 is a functional block diagram showing the component architecture of the circuitry of the monitor recorder of FIG. 4.

ECG monitoring and other functions performed by the monitor recorder 14 are provided through a micro controlled architecture. FIG. 9 is a functional block diagram showing the component architecture of the circuitry 60 of the monitor recorder 14 of FIG. 4. The circuitry 60 is externally powered through a battery provided in the non-conductive receptacle 25 (shown in FIG. 6). Both power and raw ECG signals, which originate in the pair of ECG electrodes 38, 39 (shown in FIG. 8) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions. The download station is further described infra with reference to FIG. 15.

Operation of the circuitry 60 of the monitor recorder 14 is managed by a microcontroller 61, such as the EFM32 Tiny Gecko 32-bit microcontroller, manufactured by Silicon Laboratories Inc., Austin, Tex. The microcontroller 61 has flexible energy management modes and includes a direct memory access controller and built-in analog-to-digital and digital-to-analog converters (ADC and DAC, respectively). The microcontroller 61 also includes a program memory unit containing internal flash memory that is readable and writeable. The internal flash memory can also be programmed externally. The microcontroller 61 operates under modular micro program control as specified in firmware stored in the internal flash memory. The functionality and firmware modules relating to signal processing by the microcontroller 61 are further described infra with reference to FIG. 14. The microcontroller 61 draws power externally from the battery provided on the electrode patch 15 via a pair of the electrical contacts 56. The microcontroller 61 connects to the ECG front end circuit 63 that measures raw cutaneous electrical signals using a driven reference that eliminates common mode noise, as further described infra with reference to FIG. 11.

The circuitry 60 of the monitor recorder 14 also includes a flash memory 62, which the microcontroller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

Figure 14:
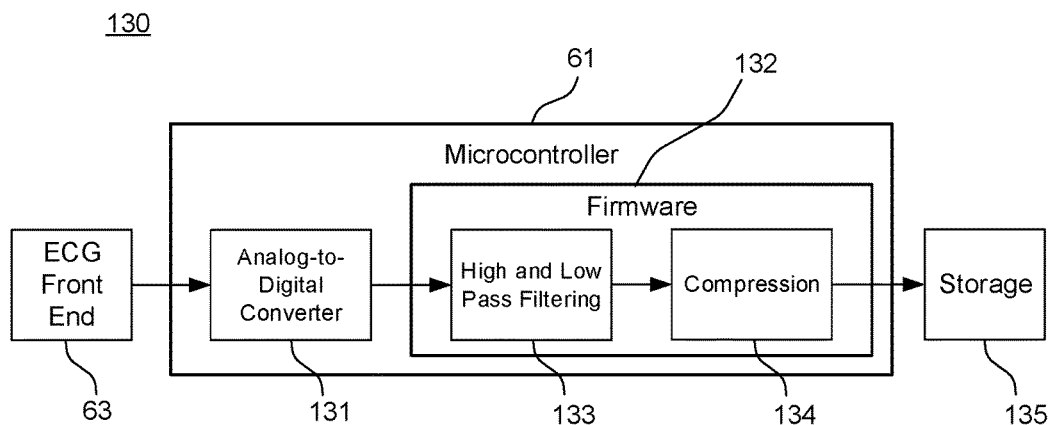
FIG. 14 is a functional block diagram showing the signal processing functionality of the microcontroller.

The microcontroller 61 includes functionality that enables the acquisition of samples of analog ECG signals, which are converted into a digital representation, as further described infra with reference to FIG. 14. In one mode, the microcontroller 61 will acquire, sample, digitize, signal process, and store digitized ECG data into available storage locations in the flash memory 62 until all memory storage locations are filled, after which the digitized ECG data needs to be downloaded or erased to restore memory capacity. Data download or erasure can also occur before all storage locations are filled, which would free up memory space sooner, albeit at the cost of possibly interrupting monitoring while downloading or erasure is performed. In another mode, the microcontroller 61 can include a loop recorder feature that will overwrite the oldest stored data once all storage locations are filled, albeit at the cost of potentially losing the stored data that was overwritten, if not previously downloaded. Still other modes of data storage and capacity recovery are possible.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the microcontroller 61 provided over one of the electrical contacts 56. The physiology sensor can include an $SpO_2$ sensor, blood pressure sensor, temperature sensor, respiratory rate sensor, glucose sensor, airflow sensor, volumetric pressure sensing, or other types of sensor or telemetric input sources. In a further embodiment, a wireless interface for interfacing with other wearable (or implantable) physiology monitors, as well as data offload and programming, can be provided as part of the circuitry 60 of the monitor recorder 14, or can be provided on the electrode patch 15 with communication with the microcontroller 61 provided over one of the electrical contacts 56.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

Figure 10:
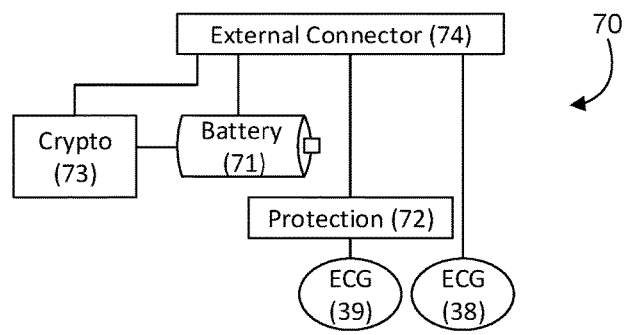
FIG. 10 is a functional block diagram showing the circuitry of the extended wear electrode patch of FIG. 4.

While the monitor recorder 14 operates under micro control, most of the electrical components of the electrode patch 15 operate passively. FIG. 10 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Also, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. This approach also enables a battery of higher capacity to be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current should the front end circuit fail.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14 and for a specific patient.

Figure 11:
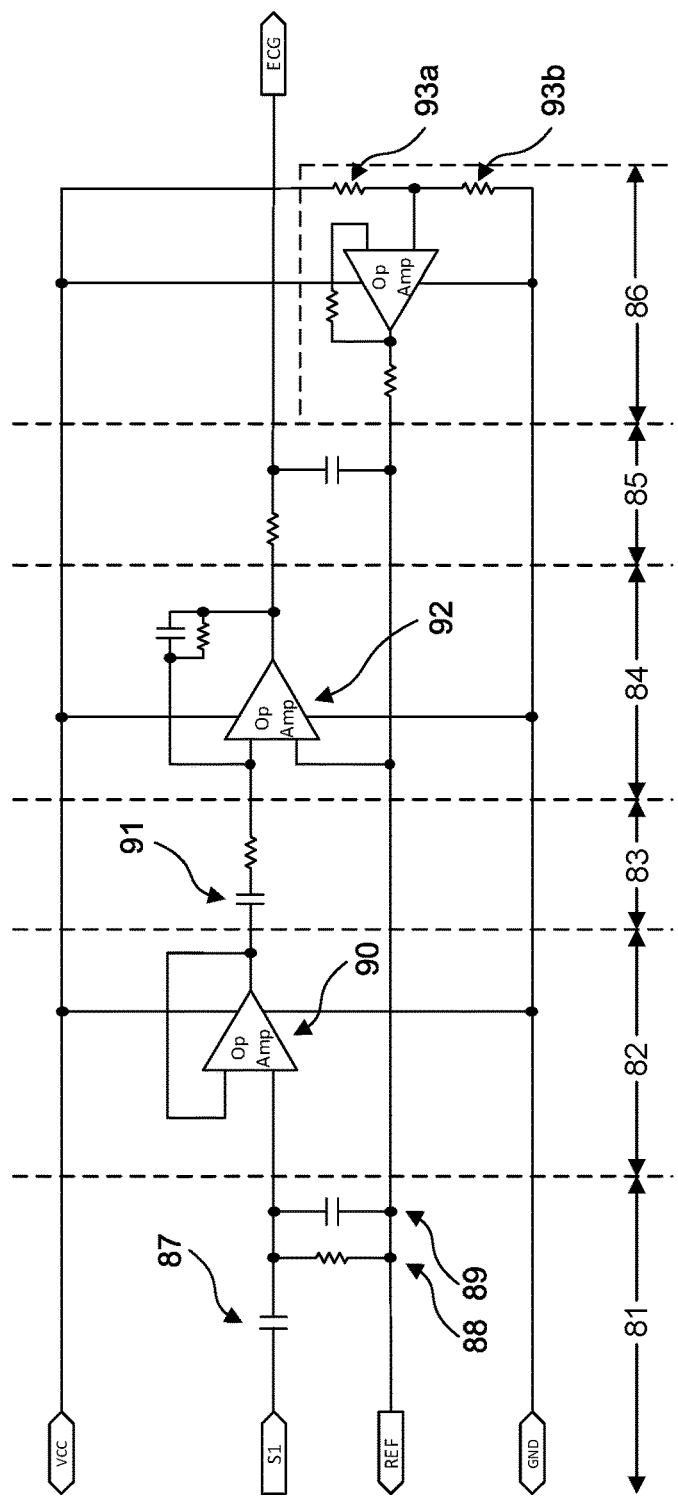
FIG. 11 is a schematic diagram showing the ECG front end circuit of the circuitry of the monitor recorder of FIG. 9.

The ECG front end circuit 63 measures raw cutaneous electrical signals using a driven reference that effectively reduces common mode noise, power supply noise and system noise, which is critical to preserving the characteristics of low amplitude cardiac action potentials, especially those signals from the atria. FIG. 11 is a schematic diagram 80 showing the ECG front end circuit 63 of the circuitry 60 of the monitor recorder 14 of FIG. 9. The ECG front end circuit 63 senses body surface potentials through a signal lead ("S1") and reference lead ("REF") that are respectively connected to the ECG electrodes of the electrode patch 15. Power is provided to the ECG front end circuit 63 through a pair of DC power leads ("VCC" and "GND"). An analog ECG signal ("ECG") representative of the electrical activity of the patient's heart over time is output, which the micro controller 11 converts to digital representation and filters, as further described infra.

The ECG front end circuit 63 is organized into five stages, a passive input filter stage 81, a unity gain voltage follower stage 82, a passive high pass filtering stage 83, a voltage amplification and active filtering stage 84, and an anti-aliasing passive filter stage 85, plus a reference generator. Each of these stages and the reference generator will now be described.

The passive input filter stage 81 includes the parasitic impedance of the ECG electrodes 38, 39 (shown in FIG. 8), the protection resistor that is included as part of the protection circuit 72 of the ECG electrode 39 (shown in FIG. 10), an AC coupling capacitor 87, a termination resistor 88, and filter capacitor 89. This stage passively shifts the frequency response poles downward there is a high electrode impedance from the patient on the signal lead S1 and reference lead REF, which reduces high frequency noise.

The unity gain voltage follower stage 82 provides a unity voltage gain that allows current amplification by an Operational Amplifier ("Op Amp") 90. In this stage, the voltage stays the same as the input, but more current is available to feed additional stages. This configuration allows a very high input impedance, so as not to disrupt the body surface potentials or the filtering effect of the previous stage.

The passive high pass filtering stage 83 is a high pass filter that removes baseline wander and any offset generated from the previous stage. Adding an AC coupling capacitor 91 after the Op Amp 90 allows the use of lower cost components, while increasing signal fidelity.

The voltage amplification and active filtering stage 84 amplifies the voltage of the input signal through Op Amp 91, while applying a low pass filter. The DC bias of the input signal is automatically centered in the highest performance input region of the Op Amp 91 because of the AC coupling capacitor 91.

The anti-aliasing passive filter stage 85 provides an anti-aliasing low pass filter. When the microcontroller 61 acquires a sample of the analog input signal, a disruption in the signal occurs as a sample and hold capacitor that is internal to the microcontroller 61 is charged to supply signal for acquisition.

The reference generator in subcircuit 86 drives a driven reference containing power supply noise and system noise to the reference lead REF. A coupling capacitor 87 is included on the signal lead S1 and a pair of resistors 93a, 93b inject system noise into the reference lead REF. The reference generator is connected directly to the patient, thereby avoiding the thermal noise of the protection resistor that is included as part of the protection circuit 72.

In contrast, conventional ECG lead configurations try to balance signal and reference lead connections. The conventional approach suffers from the introduction of differential thermal noise, lower input common mode rejection, increased power supply noise, increased system noise, and differential voltages between the patient reference and the reference used on the device that can obscure, at times, extremely, low amplitude body surface potentials.

Here, the parasitic impedance of the ECG electrodes 38, 39, the protection resistor that is included as part of the protection circuit 72 and the coupling capacitor 87 allow the reference lead REF to be connected directly to the skin's surface without any further components. As a result, the differential thermal noise problem caused by pairing protection resistors to signal and reference leads, as used in conventional approaches, is avoided.

Figure 12:
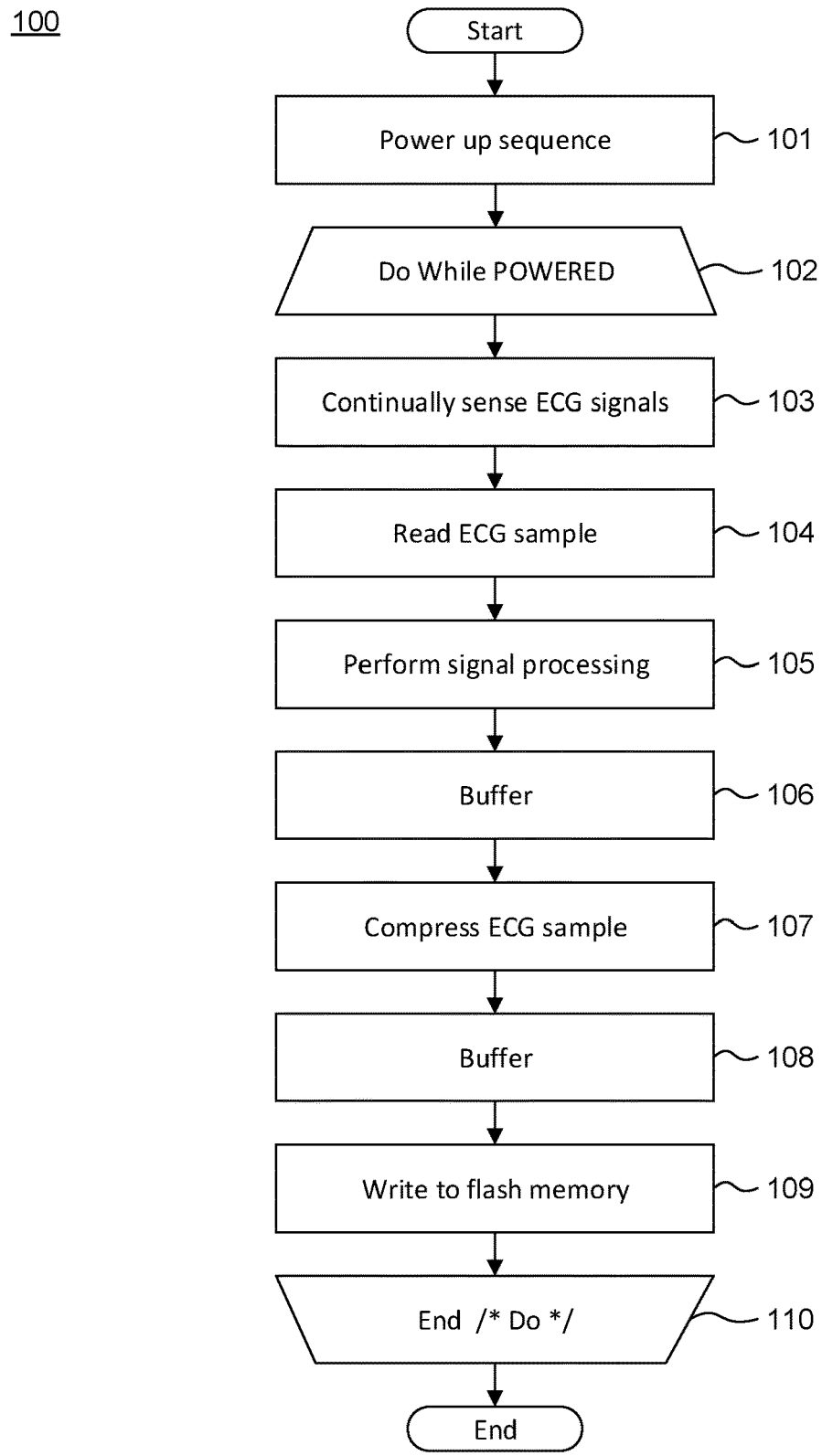
FIG. 12 is a flow diagram showing a monitor recorder-implemented method for monitoring ECG data for use in the monitor recorder of FIG. 4.

The monitor recorder 14 continuously monitors the patient's heart rate and physiology. FIG. 12 is a flow diagram showing a monitor recorder-implemented method 100 for monitoring ECG data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 13:
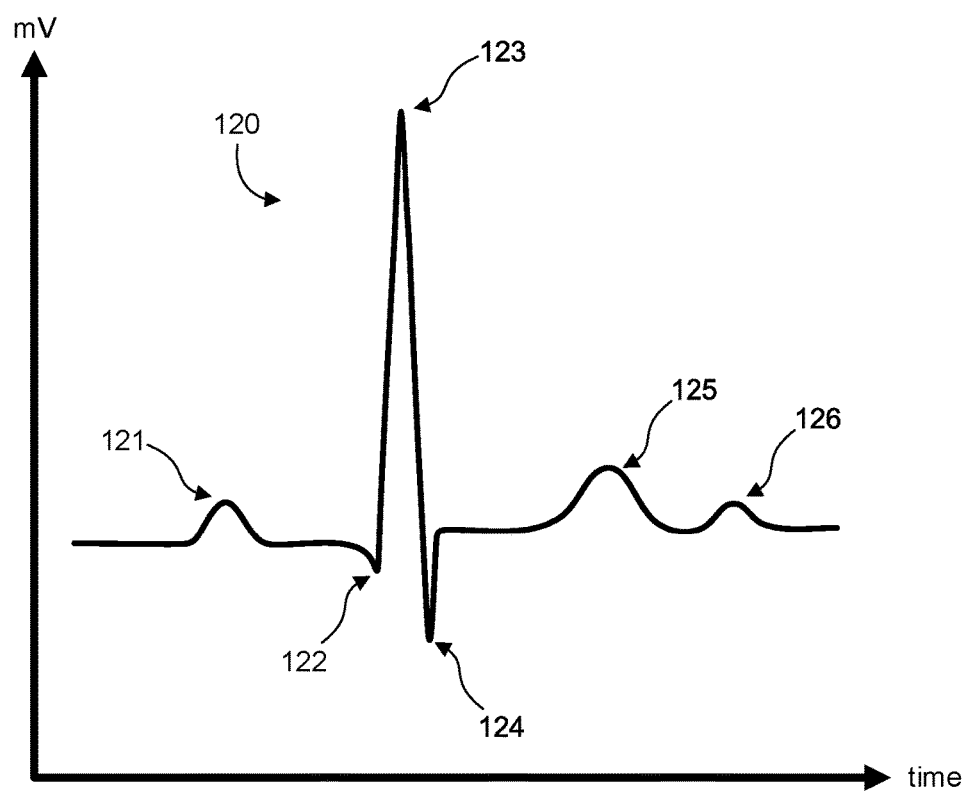
FIG. 13 is a graph showing, by way of example, a typical ECG waveform.

Following satisfactory completion of the power up sequence, an iterative processing loop (steps 102-110) is continually executed by the microcontroller 61. During each iteration (step 102) of the processing loop, the ECG frontend 63 (shown in FIG. 9) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal that is output by the ECG front end circuit 63. FIG. 13 is a graph showing, by way of example, a typical ECG waveform 120. The x-axis represents time in approximate units of tenths of a second. The y-axis represents cutaneous electrical signal strength in approximate units of millivolts. The P-wave 121 has a smooth, normally upward, that is, positive, waveform that indicates atrial depolarization. The QRS complex often begins with the downward deflection of a Q-wave 122, followed by a larger upward deflection of an R-wave 123, and terminated with a downward waveform of the S-wave 124, collectively representative of ventricular depolarization. The T-wave 125 is normally a modest upward waveform, representative of ventricular depolarization, while the U-wave 126, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the ambulatory electrocardiography monitoring patch optimized for capturing low amplitude cardiac action potential propagation described herein is medically unique and important. The long-term observation of these ECG indicia, as provided through extended wear of the wearable monitor 12, provides valuable insights to the patient's cardiac function symptoms, and overall well-being.

Referring back to FIG. 12, each sampled ECG signal, in quantized and digitized form, is processed by signal processing modules as specified in firmware (step 105), as described infra, and temporarily staged in a buffer (step 106), pending compression preparatory to storage in the flash memory 62 (step 107). Following compression, the compressed ECG digitized sample is again buffered (step 108), then written to the flash memory 62 (step 109) using the communications bus. Processing continues (step 110), so long as the monitor recorder 14 remains connected to the electrode patch 15 (and storage space remains available in the flash memory 62), after which the processing loop is exited (step 110) and execution terminates. Still other operations and steps are possible.

The microcontroller 61 operates under modular micro program control as specified in firmware, and the program control includes processing of the analog ECG signal output by the ECG front end circuit 63. FIG. 14 is a functional block diagram showing the signal processing functionality 130 of the microcontroller 61. The microcontroller 61 operates under modular micro program control as specified in firmware 132. The firmware modules 132 include high and low pass filtering 133, and compression 134. Other modules are possible. The microcontroller 61 has a built-in ADC, although ADC functionality could also be provided in the firmware 132.

The ECG front end circuit 63 first outputs an analog ECG signal, which the ADC 131 acquires, samples and converts into an uncompressed digital representation. The microcontroller 61 includes one or more firmware modules 133 that perform filtering. In one embodiment, three low pass filters and two high pass filters are used. Following filtering, the digital representation of the cardiac activation wave front amplitudes are compressed by a compression module 134 before being written out to storage 135, as further described infra beginning with reference to FIG. 22.

Figure 15:
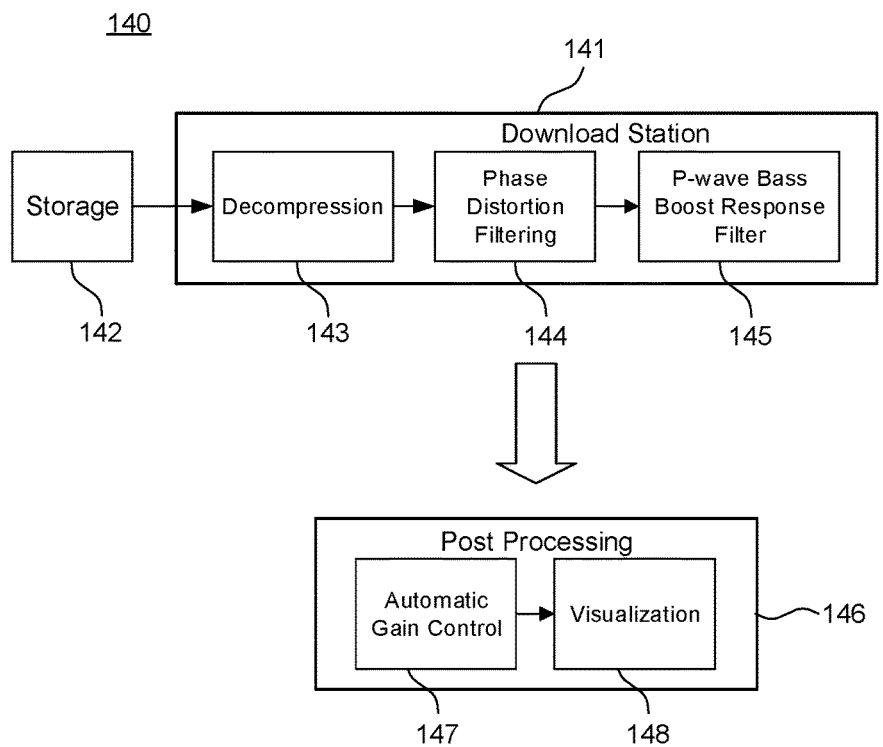
FIG. 15 is a functional block diagram showing the operations performed by the download station.

The download station executes a communications or offload program ("Offload") or similar program that interacts with the monitor recorder 14 via the external connector 65 to retrieve the stored ECG monitoring data. FIG. 15 is a functional block diagram showing the operations 140 performed by the download station. The download station could be a server, personal computer, tablet or handheld computer, smart mobile device, or purpose-built programmer designed specific to the task of interfacing with a monitor recorder 14. Still other forms of download station are possible, including download stations connected through wireless interfacing using, for instance, a smart phone connected to the monitor recorder 14 through Bluetooth or Wi-Fi.

The download station is responsible for offloading stored ECG monitoring data from a monitor recorder 14 and includes an electro mechanical docking interface by which the monitor recorder 14 is connected at the external connector 65. The download station operates under programmable control as specified in software 141. The stored ECG monitoring data retrieved from storage 142 on a monitor recorder 14 is first decompressed by a decompression module 143, which decompresses the stored ECG monitoring data back into an uncompressed digital time series representation of the raw ECG signal that is more suited to signal processing than a compressed signal. The retrieved ECG monitoring data may be stored into local storage for archival purposes, either in original compressed form, or as an uncompressed time series.

The download station can include an array of filtering modules. For instance, a set of phase distortion filtering tools 144 may be provided, where corresponding software filters can be provided for each filter implemented in the firmware executed by the microcontroller 61. The digital signals are run through the software filters in a reverse direction to remove phase distortion. For instance, a 45 Hertz high pass filter in firmware may have a matching reverse 45 Hertz high pass filter in software. Most of the phase distortion is corrected, that is, canceled to eliminate noise at the set frequency, but data at other frequencies in the waveform remain unaltered. As well, bidirectional impulse infinite response (IIR) high pass filters and reverse direction (symmetric) IIR low pass filters can be provided. Data is run through these filters first in a forward direction, then in a reverse direction, which generates a square of the response and cancels out any phase distortion. This type of signal processing is particularly helpful with improving the display of the ST-segment by removing low frequency noise.

The download station can also include filtering modules specifically intended to enhance P-wave content. For instance, a P-wave base boost filter 145, which is a form of pre-emphasis filter, can be applied to the signal to restore missing frequency content or to correct phase distortion. Still other filters and types of signal processing are possible.

An automatic gain control (AGC) module 147 can be provided as part of a suite of post-processing modules 146 that include ECG signal visualization 148. The AGC module 147 adjusts the digital signals to a usable level based on peak or average signal level or other metric. AGC is particularly critical to single-lead ECG monitors, where physical factors, such as the tilt of the heart or region of placement on the body, can affect the electrical field generated. On three-lead Holter monitors, the leads are oriented in vertical, horizontal and diagonal directions. As a result, the horizontal and diagonal leads may be higher amplitude and ECG interpretation will be based on one or both of the higher amplitude leads. In contrast, the electrocardiography monitor 12 has only a single lead that is oriented in the vertical direction, so variations in amplitude will be wider than available with multi-lead monitors, which have alternate leads to fall back upon.

In addition, AGC may be necessary to maintain compatibility with existing ECG interpretation software, which is typically calibrated for multi-lead ECG monitors for viewing signals over a narrow range of amplitudes. Through the AGC module 147, the gain of signals recorded by the monitor recorder 14 of the electrocardiography monitor 12 can be attenuated up (or down) to work with FDA-approved commercially available ECG interpretation.

AGC can be implemented in a fixed fashion that is uniformly applied to all signals in an ECG recording, adjusted as appropriate on a recording-by-recording basis. Typically, a fixed AGC value is calculated based on how an ECG recording is received to preserve the amplitude relationship between the signals. Alternatively, AGC can be varied dynamically throughout an ECG recording, where signals in different segments of an ECG recording are amplified up (or down) by differing amounts of gain or to maximize the number of signals appearing within a desired range.

Figure 27:
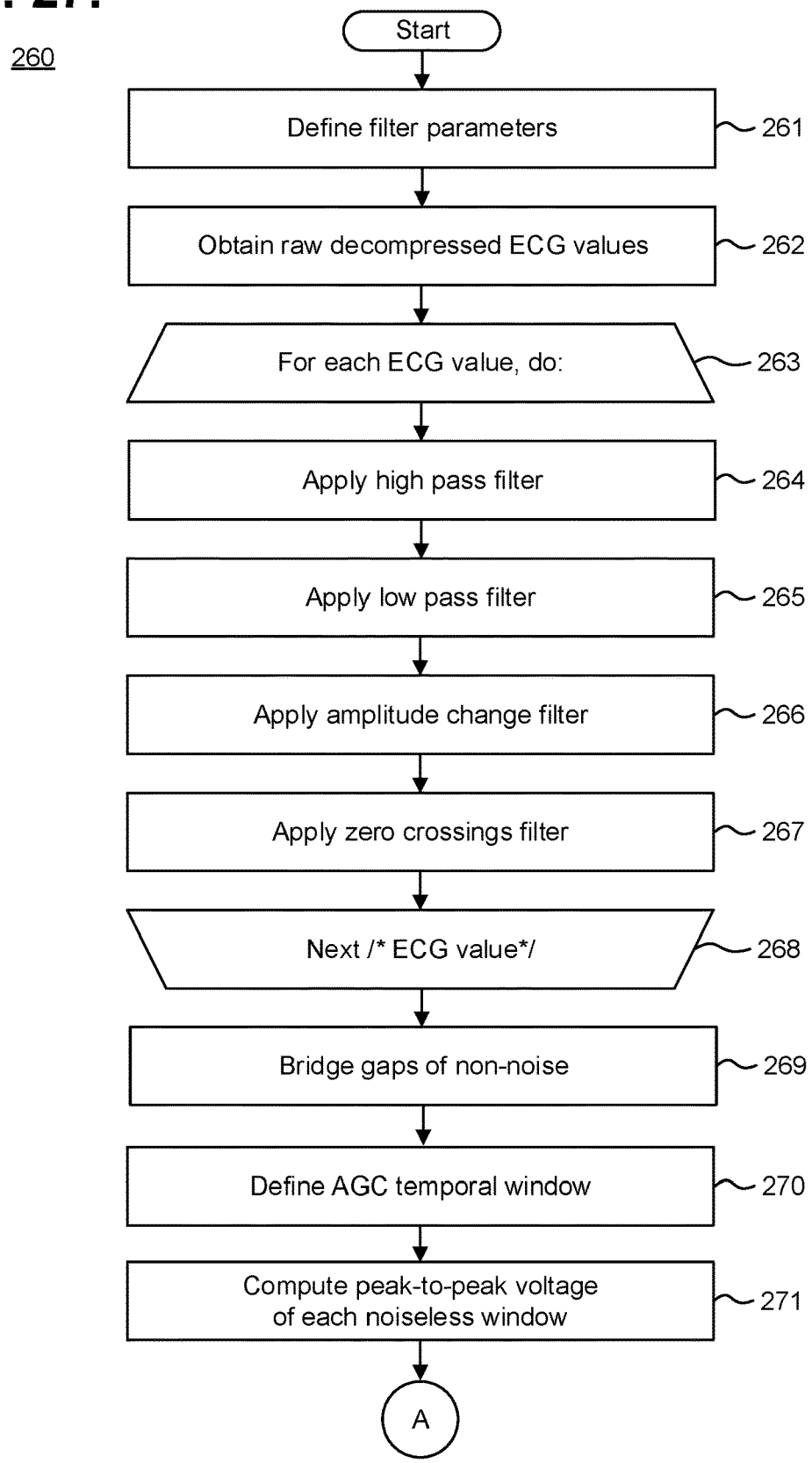
FIG. 27 is a flow diagram showing a routine for providing automatic gain control through middleware.

Typically, the monitor recorder 14 will record a high resolution, low frequency signal for the P-wave segment. However, for some patients, the result may still be a visually small signal that can complicate diagnostic overread. Although high signal resolution is present, the unaided eye will normally be unable to discern the P-wave segment with sufficient detail. Therefore, gaining the signal can be critical to visually depicting P-wave details with proper clarity, which can be automatically performed by middleware after a set of ECG signals has been downloaded from a monitor recorder 14 and decompressed. FIG. 27 is a flow diagram showing a routine 260 for providing automatic gain control through middleware. Automatic gain control is generally provided through an AGC module 147 that is implemented as part of a suite of post-processing modules 146, although automatic gain control could also be provided through standalone software or as part of other forms of ECG visualization and interpretation software.

The AGC technique works most efficaciously with a raw (decompressed) ECG signal with low noise and high resolution. Noise amplitude differs from the signal amplitude, so noise must be excluded from the gain calculations. Automatic gain control applied to a high noise signal will only exacerbate noise content and be self-defeating. Thus, the routine 260 first applies a set of filters to identify noise in the signal (steps 263-268). The noise is then marked and subsequently ignored, except as noted, during automatic signal gain (steps 272-275). During noise filtering, a set of noise filter parameters is first defined (step 261). The noise filter parameters are dependent upon the type of filter employed, as set forth infra. The set of raw decompressed ECG values are obtained (step 262).

Each ECG value is processed (step 263) in an iterative loop (steps 263-268). For each ECG value (step 263), four types of noise filters are applied to the ECG values, a high pass filter (step 264), a low pass filter (step 265), an amplitude change filter (step 266), and a zero-crossings filter (step 267). As used herein, "peak-to-peak" means the difference between the maximum and minimum voltage during some particular time period. Ordinarily, peak ECG voltage occurs at the top of the upward deflection of the R-wave 123 (shown in FIG. 13), although other peak ECG voltage markers could be used, such as the top of the upward deflection of consecutive P-waves 121, so long as the same two types of peak ECG voltages are compared. The high pass filter (step 264) marks signals that fall below as pre-defined threshold as noise. The filter is triggered when eight seconds or more of sub-0.2 mV signals, peak-to-peak, are detected, and a span of about 120 seconds of the signal is marked as noise, starting from the eight-second point. Other high pass threshold values and filtration durations could be employed. Note that the noise markers are ignored for purposes of automatic signal gain. The low pass filter (step 265) marks signals that fall above a pre-defined threshold as noise. The filter is triggered whenever supra-20 mV signals, peak-to-peak, are detected, and a span of about 60 seconds is marked as noise, 30 seconds preceding and 30 seconds following the first detection of noise. Other threshold values and filtration durations could be employed. The amplitude change filter (step 266) marks signals whose difference from immediately preceding signals exceed a pre-defined threshold as noise. The filter is triggered when the peak-to-peak signal strengths of adjoining three-second segments change by more than 300%, that is, triples in strength, and a span of about 30 seconds is marked as noise, starting from the onset of noise. Other threshold values and filtration durations could be employed. Finally, the zero-crossings filter (step 267) marks signals that cross zero mV, from either direction, more than a pre-defined threshold as noise. The filter is triggered when the signal crosses zero more than ten times in one second, and a span of about 15 seconds is marked as noise, starting with the onset of noise. Other zero-crossings threshold values and filtration durations could be employed. Other types of noise filters are also possible. Each remaining ECG value is processed (step 268).

Automatic gain is applied to enhance an ECG signal to help display important details, especially visually depicting P-wave details. Automatic gain is applied to the ECG signals after noise has been marked (steps 263-268), although noise filtering, while recommended and desirable, could be skipped. Finally, gaps of non-noise are bridged (step 269), so that the displayed ECG signal appears to be a continuous signal. The appearance of continuity of signal can be particularly important when long gaps of noise are present. Note that noise in the signal is only marked. The raw, unfiltered signal, complete with noise, can still be retrieved and displayed, if desired.

Initially, a temporal window for AGC is defined (step 270). The temporal window has to be long enough to capture at least one heart beat; a five-second temporal window is used, although other durations are possible. The peak-to-peak voltage of each noiseless window is computed (step 271). As the goal is to try to place or center as many peak-to-peak voltages in the preferred range as practicable, a single gain factor is applied to the entire signal such that the average signal falls in the center of the preferred range. Alternatively, other statistical values could be used to represent the correlation of the peak-to-peak voltages in the preferred range, either in lieu of or in addition to the average voltage, such as maximum or minimum observed voltage, mean voltage, and so on.

Each ECG value is then processed (step 273) in an iterative loop (steps 273-275). The ECG values are dynamically gained (step 274). In one embodiment, the preferred range falls from about 2 mV to 10 mV, although other values could be chosen. Each remaining ECG value is processed (step 275).

Figure 16A:
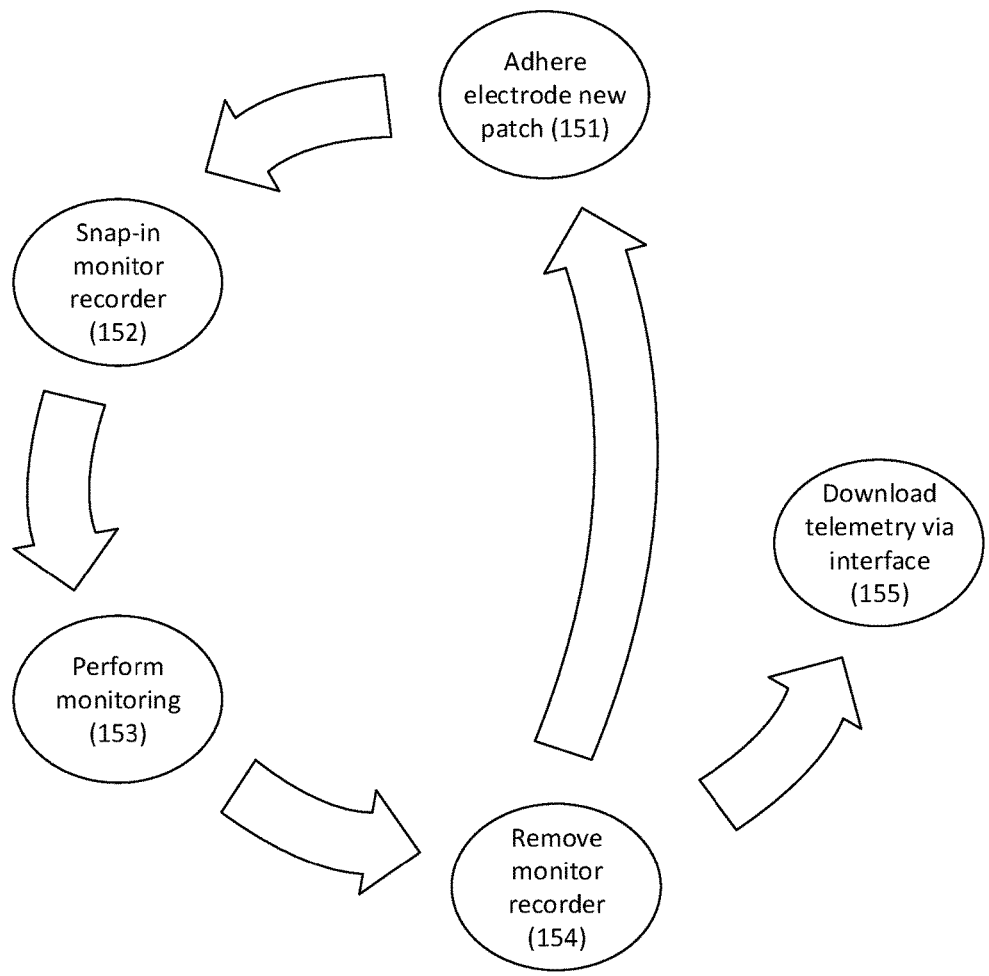
FIGS. 16A-C are functional block diagrams respectively showing practical uses of the extended wear electrocardiography monitors of FIGS. 1 and 2.
Figure 16B:
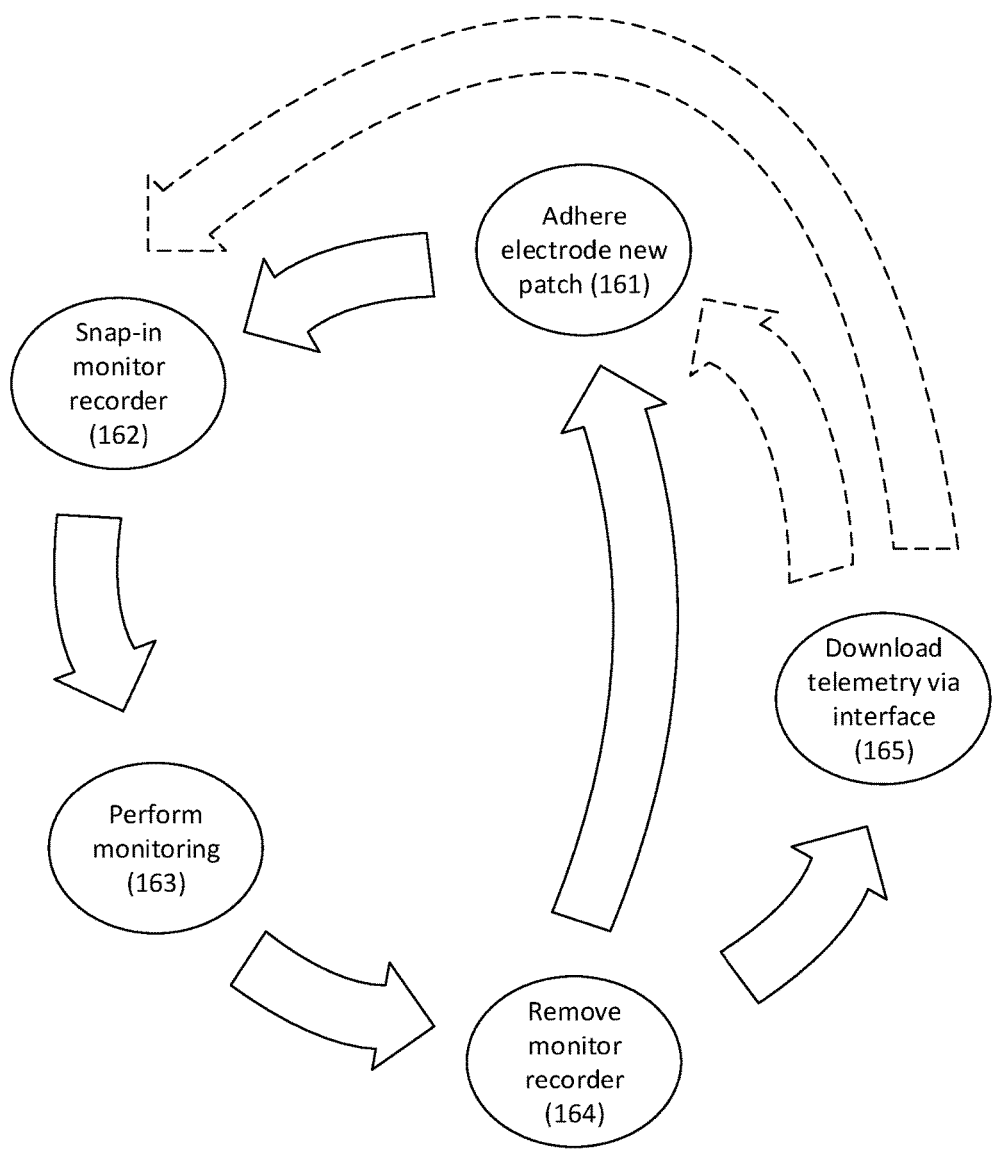
Figure 16C:
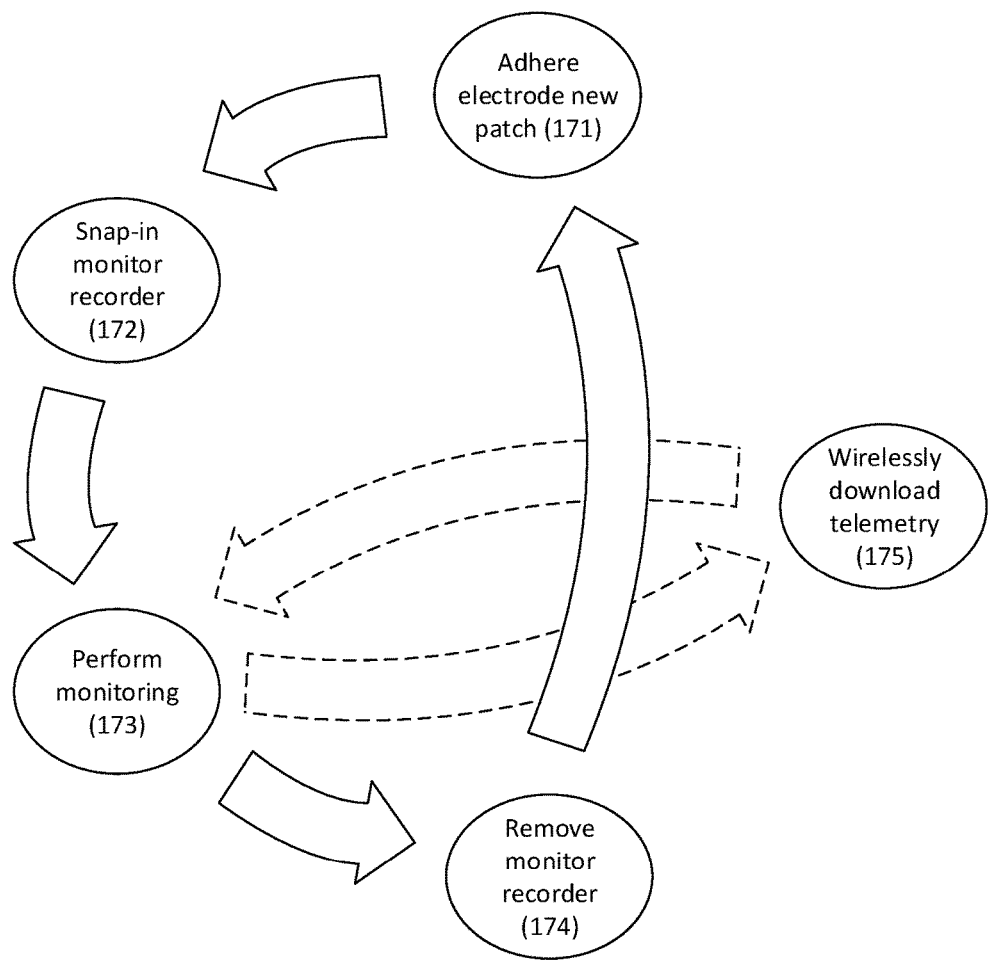

Conventional ECG monitors, like Holter monitors, invariably require specialized training on proper placement of leads and on the operation of recording apparatuses, plus support equipment purpose-built to retrieve, convert, and store ECG monitoring data. In contrast, the electrocardiography monitor 12 simplifies monitoring from end to end, starting with placement, then with use, and finally with data retrieval. FIGS. 16A-C are functional block diagrams respectively showing practical uses 150, 160, 170 of the extended wear electrocardiography monitors 12 of FIGS. 1 and 2. The combination of a flexible extended wear electrode patch and a removable reusable (or single use) monitor recorder empowers physicians and patients alike with the ability to readily perform long-term ambulatory monitoring of the ECG and physiology.

Especially when compared to existing Holter-type monitors and monitoring patches placed in the upper pectoral region, the electrocardiography monitor 12 offers superior patient comfort, convenience and user-friendliness. To start, the electrode patch 15 is specifically designed for ease of use by a patient (or caregiver); assistance by professional medical personnel is not required. Moreover, the patient is free to replace the electrode patch 15 at any time and need not wait for a doctor's appointment to have a new electrode patch 15 placed. In addition, the monitor recorder 14 operates automatically and the patient only need snap the monitor recorder 14 into place on the electrode patch 15 to initiate ECG monitoring. Thus, the synergistic combination of the electrode patch 15 and monitor recorder 14 makes the use of the electrocardiography monitor 12 a reliable and virtually foolproof way to monitor a patient's ECG and physiology for an extended, or even open-ended, period of time.

In simplest form, extended wear monitoring can be performed by using the same monitor recorder 14 inserted into a succession of fresh new electrode patches 15. As needed, the electrode patch 15 can be replaced by the patient (or caregiver) with a fresh new electrode patch 15 throughout the overall monitoring period. Referring first to FIG. 16A, at the outset of monitoring, a patient adheres a new electrode patch 15 in a location at the sternal midline 16 (or immediately to either side of the sternum 13) oriented top-to-bottom (step 151). The placement of the wearable monitor in a location at the sternal midline (or immediately to either side of the sternum), with its unique narrow "hourglass"-like shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms.

Placement involves simply adhering the electrode patch 15 on the skin along the sternal midline 16 (or immediately to either side of the sternum 13). Patients can easily be taught to find the physical landmarks on the body necessary for proper placement of the electrode patch 15. The physical landmarks are locations on the surface of the body that are already familiar to patients, including the inter-mammary cleft between the breasts above the manubrium (particularly easily locatable by women and gynecomastic men), the sternal notch immediately above the manubrium, and the Xiphoid process located at the bottom of the sternum. Empowering patients with the knowledge to place the electrode patch 15 in the right place ensures that the ECG electrodes will be correctly positioned on the skin, no matter the number of times that the electrode patch 15 is replaced.

A monitor recorder 14 is snapped into the non-conductive receptacle 25 on the outward-facing surface of the electrode patch 15 (step 152). The monitor recorder 14 draws power externally from a battery provided in the non-conductive receptacle 25. In addition, the battery is replaced each time that a fresh new electrode patch 15 is placed on the skin, which ensures that the monitor recorder 14 is always operating with a fresh power supply and minimizing the chances of a loss of monitoring continuity due to a depleted battery source.

By default, the monitor recorder 14 automatically initiates monitoring upon sensing body surface potentials through the pair of ECG electrodes (step 153). In a further embodiment, the monitor recorder 14 can be configured for manual operation, such as by using the tactile feedback button 66 on the outside of the sealed housing 50, or other user-operable control. In an even further embodiment, the monitor recorder 14 can be configured for remotely-controlled operation by equipping the monitor recorder 14 with a wireless transceiver, such as described in commonly-assigned U.S. Pat. No. 9,433,367, issued Sep. 6, 2016, the disclosure of which is incorporated by reference. The wireless transceiver allows wearable or mobile communications devices to wirelessly interface with the monitor recorder 14.

A key feature of the extended wear electrocardiography monitor 12 is the ability to monitor ECG and physiological data for an extended period of time, which can be well in excess of the 14 days currently pitched as being achievable by conventional ECG monitoring approaches. In a further embodiment, ECG monitoring can even be performed over an open-ended time period, as further explained infra. The monitor recorder 14 is reusable and, if so desired, can be transferred to successive electrode patches 15 to ensure continuity of monitoring. At any point during ECG monitoring, a patient (or caregiver) can remove the monitor recorder 14 (step 154) and replace the electrode patch 15 currently being worn with a fresh new electrode patch 15 (step 151). The electrode patch 15 may need to be replaced for any number of reasons. For instance, the electrode patch 15 may be starting to come off after a period of wear or the patient may have skin that is susceptible to itching or irritation. The wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose.

Following replacement, the monitor recorder 14 is again snapped into the electrode patch 15 (step 152) and monitoring resumes (step 153). The ability to transfer the same monitor recorder 14 to successive electrode patches 15 during a period of extended wear monitoring is advantageous not to just diagnose cardiac rhythm disorders and other physiological events of potential concern, but to do extremely long term monitoring, such as following up on cardiac surgery, ablation procedures, or medical device implantation. In these cases, several weeks of monitoring or more may be needed. In addition, some IMDs, such as pacemakers or implantable cardioverter defibrillators, incorporate a loop recorder that will capture cardiac events over a fixed time window. If the telemetry recorded by the IMD is not downloaded in time, cardiac events that occurred at a time preceding the fixed time window will be overwritten by the IMD and therefore lost. The monitor recorder 14 provides continuity of monitoring that acts to prevent loss of cardiac event data. In a further embodiment, the firmware executed by the microcontroller 61 of the monitor recorder 14 can be optimized for minimal power consumption and additional flash memory for storing monitoring data can be added to achieve a multi-week monitor recorder 14 that can be snapped into a fresh new electrode patch 15 every seven days, or other interval, for weeks or even months on end.

Upon the conclusion of monitoring, the monitor recorder 14 is removed (step 154) and recorded ECG and physiological telemetry are downloaded (step 155). For instance, a download station can be physically interfaced to the external connector 65 of the monitor recorder 14 to initiate and conduct downloading, as described supra with reference to FIG. 15.

In a further embodiment, the monitoring period can be of indeterminate duration. Referring next to FIG. 16B, a similar series of operations are followed with respect to replacement of electrode patches 15, reinsertion of the same monitor recorder 14, and eventual download of ECG and physiological telemetry (steps 161-165), as described supra with reference to FIG. 16A. However, the flash memory 62 (shown in FIG. 9) in the circuitry 60 of the monitor recorder 14 has a finite capacity. Following successful downloading of stored data, the flash memory 62 can be cleared to restore storage capacity and monitoring can resume once more, either by first adhering a new electrode patch 15 (step 161) or by snapping the monitor recorder 14 into an already-adhered electrode patch 15 (step 162). The foregoing expanded series of operations, to include reuse of the same monitor recorder 14 following data download, allows monitoring to continue indefinitely and without the kinds of interruptions that often affect conventional approaches, including the retrieval of monitoring data only by first making an appointment with a medical professional.

In a still further embodiment, when the monitor recorder 14 is equipped with a wireless transceiver, the use of a download station can be skipped. Referring last to FIG. 16C, a similar series of operations are followed with respect to replacement of electrode patches 15 and reinsertion of the same monitor recorder 14 (steps 171-174), as described supra with reference to FIG. 16A. However, recorded ECG and physiological telemetry are downloaded wirelessly (step 175), such as described in commonly-assigned U.S. patent application Ser. No. 14/082,071, cited supra. The recorded ECG and physiological telemetry can even be downloaded wirelessly directly from a monitor recorder 14 during monitoring while still snapped into the non-conductive receptacle 25 on the electrode patch 15. The wireless interfacing enables monitoring to continue for an open-ended period of time, as the downloading of the recorded ECG and physiological telemetry will continually free up onboard storage space. Further, wireless interfacing simplifies patient use, as the patient (or caregiver) only need worry about placing (and replacing) electrode patches 15 and inserting the monitor recorder 14. Still other forms of practical use of the extended wear electrocardiography monitors 12 are possible.

Figure 17:
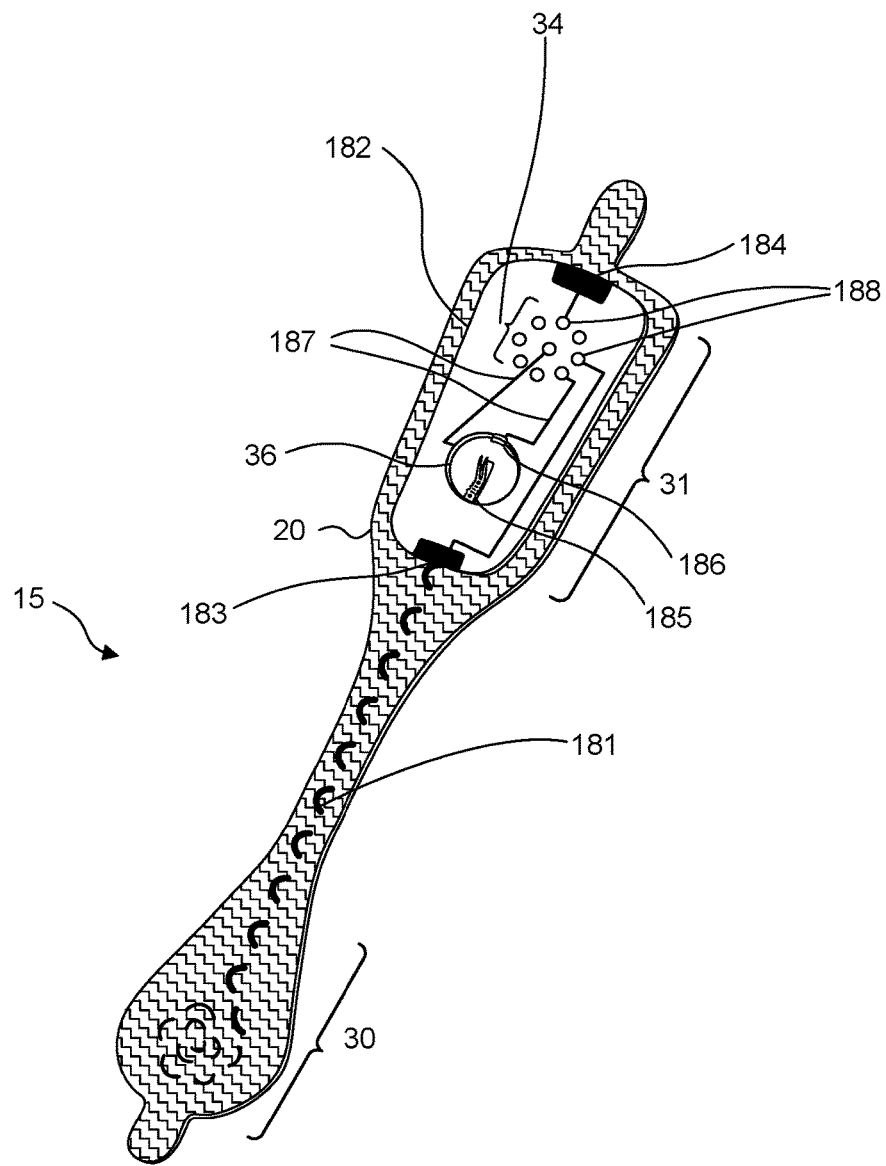
FIG. 17 is a perspective view of an extended wear electrode patch with a flexile wire electrode assembly in accordance with a still further embodiment.

The circuit trace and ECG electrodes components of the electrode patch 15 can be structurally simplified. In a still further embodiment, the flexible circuit 32 (shown in FIG. 5) and distal ECG electrode 38 and proximal ECG electrode 39 (shown in FIG. 6) are replaced with a pair of interlaced flexile wires. The interlacing of flexile wires through the flexible backing 20 reduces both manufacturing costs and environmental impact, as further described infra. The flexible circuit and ECG electrodes are replaced with a pair of flexile wires that serve as both electrode circuit traces and electrode signal pickups. FIG. 17 is a perspective view 180 of an extended wear electrode patch 15 with a flexile wire electrode assembly in accordance with a still further embodiment. The flexible backing 20 maintains the unique narrow "hourglass"-like shape that aids long term extended wear, particularly in women, as described supra with reference to FIG. 4. For clarity, the non-conductive receptacle 25 is omitted to show the exposed battery printed circuit board 182 that is adhered underneath the non-conductive receptacle 25 to the proximal end 31 of the flexible backing 20. Instead of employing flexible circuits, a pair of flexile wires are separately interlaced or sewn into the flexible backing 20 to serve as circuit connections for an anode electrode lead and for a cathode electrode lead.

To form a distal electrode assembly, a distal wire 181 is interlaced into the distal end 30 of the flexible backing 20, continues along an axial path through the narrow longitudinal midsection of the elongated strip, and electrically connects to the battery printed circuit board 182 on the proximal end 31 of the flexible backing 20. The distal wire 181 is connected to the battery printed circuit board 182 by stripping the distal wire 181 of insulation, if applicable, and interlacing or sewing the uninsulated end of the distal wire 181 directly into an exposed circuit trace 183. The distal wire-to-battery printed circuit board connection can be made, for instance, by back stitching the distal wire 181 back and forth across the edge of the battery printed circuit board 182. Similarly, to form a proximal electrode assembly, a proximal wire (not shown) is interlaced into the proximal end 31 of the flexible backing 20. The proximal wire is connected to the battery printed circuit board 182 by stripping the proximal wire of insulation, if applicable, and interlacing or sewing the uninsulated end of the proximal wire directly into an exposed circuit trace 184. The resulting flexile wire connections both establish electrical connections and help to affix the battery printed circuit board 182 to the flexible backing 20.

The battery printed circuit board 182 is provided with a battery compartment 36. A set of electrical pads 34 are formed on the battery printed circuit board 182. The electrical pads 34 electrically interface the battery printed circuit board 182 with a monitor recorder 14 when fitted into the non-conductive receptacle 25. The battery compartment 36 contains a spring 185 and a clasp 186, or similar assembly, to hold a battery (not shown) in place and electrically interfaces the battery to the electrical pads 34 through a pair battery leads 187 for powering the electrocardiography monitor 14. Other types of battery compartment are possible. The battery contained within the battery compartment 36 can be replaceable, rechargeable, or disposable.

In a yet further embodiment, the circuit board and non-conductive receptacle 25 are replaced by a combined housing that includes a battery compartment and a plurality of electrical pads. The housing can be affixed to the proximal end of the elongated strip through the interlacing or sewing of the flexile wires or other wires or threads.

The core of the flexile wires may be made from a solid, stranded, or braided conductive metal or metal compounds. In general, a solid wire will be less flexible than a stranded wire with the same total cross-sectional area, but will provide more mechanical rigidity than the stranded wire. The conductive core may be copper, aluminum, silver, or other material. The pair of the flexile wires may be provided as insulated wire. In one embodiment, the flexile wires are made from a magnet wire from Belden Cable, catalogue number 8051, with a solid core of AWG 22 with bare copper as conductor material and insulated by polyurethane or nylon. Still other types of flexile wires are possible. In a further embodiment, conductive ink or graphene can be used to print electrical connections, either in combination with or in place of the flexile wires.

Figure 18:
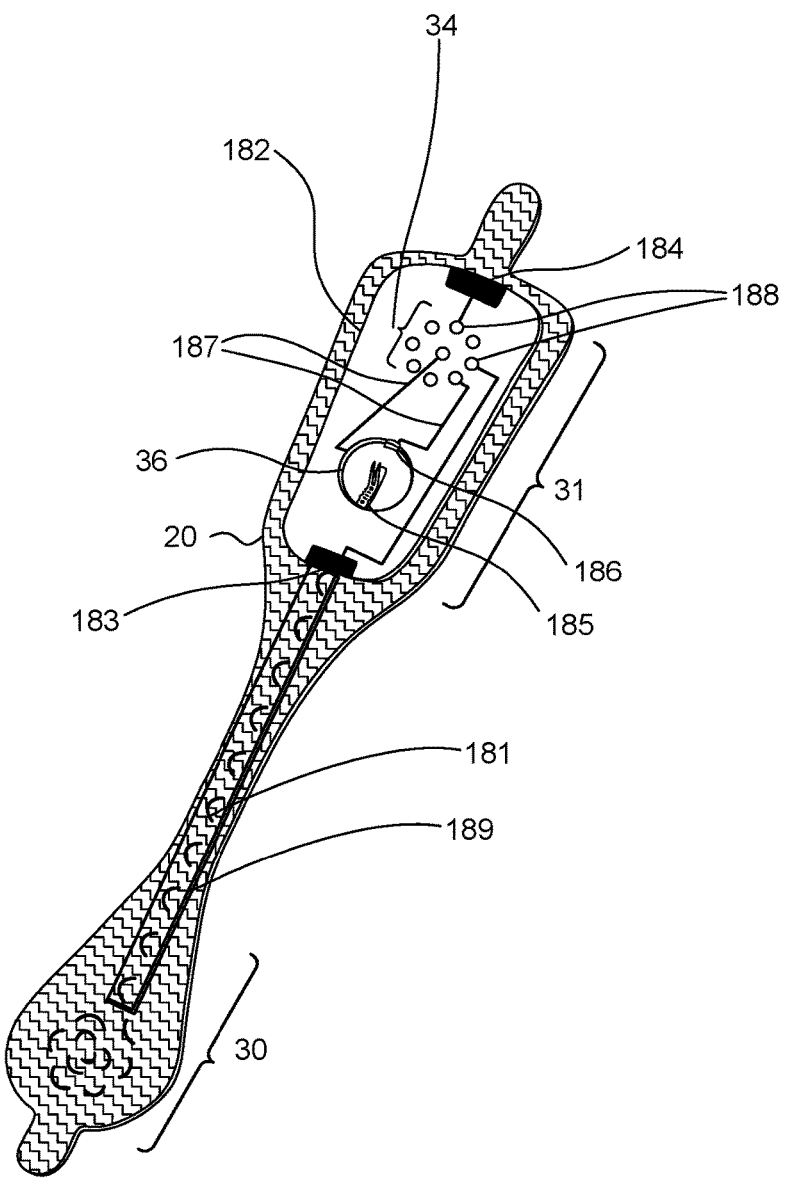
FIG. 18 is perspective view of the flexile wire electrode assembly from FIG. 17, with a layer of insulating material shielding a bare distal wire around the midsection of the flexible backing.

In a still further embodiment, the flexile wires are uninsulated. FIG. 18 is perspective view of the flexile wire electrode assembly from FIG. 17, with a layer of insulating material 189 shielding a bare uninsulated distal wire 181 around the midsection on the contact side of the flexible backing. On the contact side of the proximal and distal ends of the flexible backing, only the portions of the flexile wires serving as electrode signal pickups are electrically exposed and the rest of the flexile wire on the contact side outside of the proximal and distal ends are shielded from electrical contact. The bare uninsulated distal wire 181 may be insulated using a layer of plastic, rubber-like polymers, or varnish, or by an additional layer of gauze or adhesive (or non-adhesive) gel. The bare uninsulated wire 181 on the non-contact side of the flexible backing may be insulated or can simply be left uninsulated.

Figure 19:
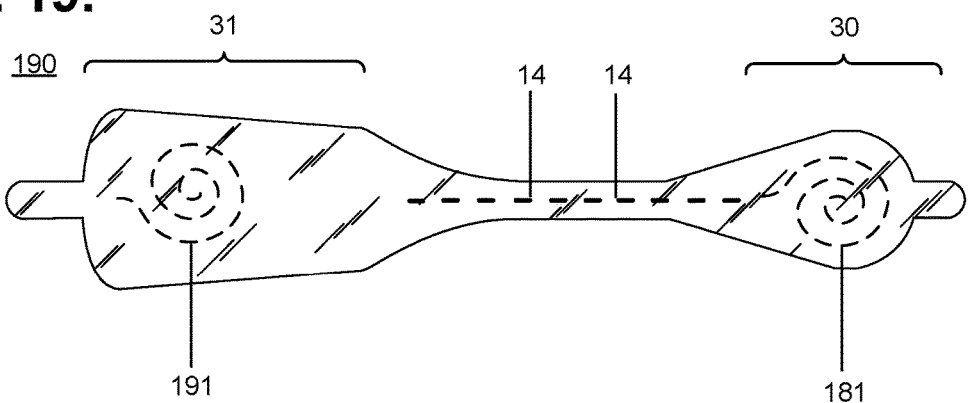
FIG. 19 is a bottom view of the flexile wire electrode assembly as shown in FIG. 17.

Both end portions of the pair of flexile wires are typically placed uninsulated on the contact surface of the flexible backing 20 to form a pair of electrode signal pickups. FIG. 19 is a bottom view 190 of the flexile wire electrode assembly as shown in FIG. 17. When adhered to the skin during use, the uninsulated end portions of the distal wire 181 and the proximal wire 191 enable the monitor recorder 14 to measure dermal electrical potential differentials. At the proximal and distal ends of the flexible backing 20, the uninsulated end portions of the flexile wires may be configured into an appropriate pattern to provide an electrode signal pickup, which would typically be a spiral shape formed by guiding the flexile wire along an inwardly spiraling pattern. The surface area of the electrode pickups can also be variable, such as by selectively removing some or all of the insulation on the contact surface. For example, an electrode signal pickup arranged by sewing insulated flexile wire in a spiral pattern could have a crescent-shaped cutout of uninsulated flexile wire facing towards the signal source.

Figure 20:
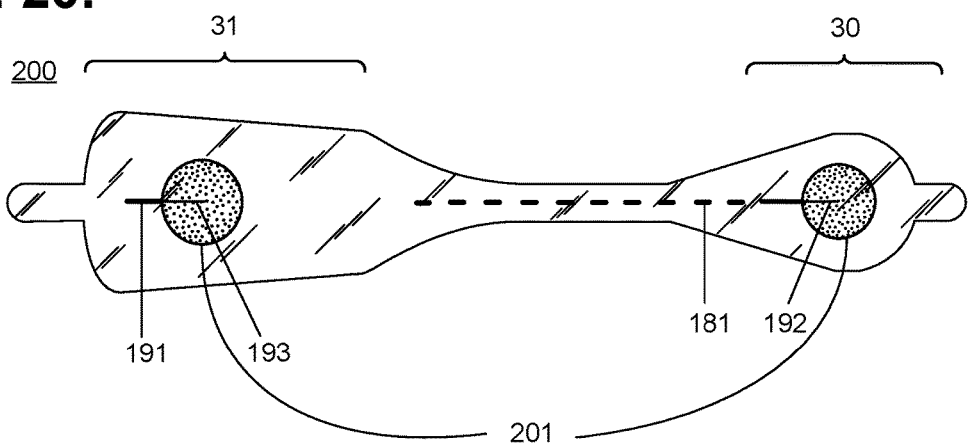
FIG. 20 is a bottom view of a flexile wire electrode assembly in accordance with a still yet further embodiment.

In a still yet further embodiment, the flexile wires are left freely riding on the contact surfaces on the distal and proximal ends of the flexible backing, rather than being interlaced into the ends of the flexible backing 20. FIG. 20 is a bottom view 200 of a flexile wire electrode assembly in accordance with a still yet further embodiment. The distal wire 181 is interlaced onto the midsection and extends an exposed end portion 192 onto the distal end 30. The proximal wire 191 extends an exposed end portion 193 onto the proximal end 31. The exposed end portions 192 and 193, not shielded with insulation, are further embedded within an electrically conductive adhesive 201. The adhesive 201 makes contact to skin during use and conducts skin electrical potentials to the monitor recorder 14 (not shown) via the flexile wires. The adhesive 201 can be formed from electrically conductive, non-irritating adhesive, such as hydrocolloid.

Figure 21:
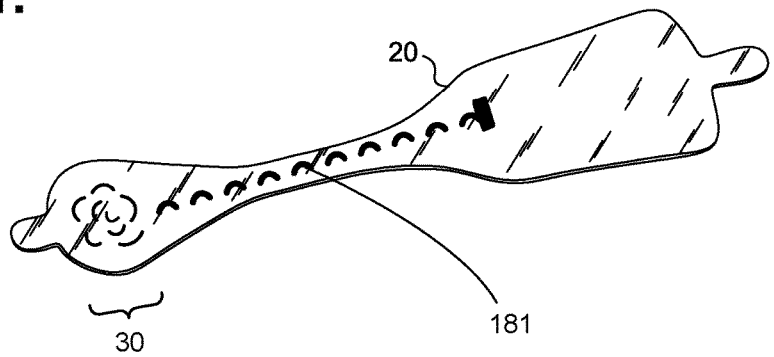
FIG. 21 is a perspective view showing the longitudinal midsection of the flexible backing of the electrode assembly from FIG. 17.

The distal wire 181 is interlaced or sewn through the longitudinal midsection of the flexible backing 20 and takes the place of the flexible circuit 32. FIG. 21 is a perspective view showing the longitudinal midsection of the flexible backing of the electrode assembly from FIG. 17. Various stitching patterns may be adopted to provide a proper combination of rigidity and flexibility. In simplest form, the distal wire 181 can be manually threaded through a plurality of holes provided at regularly-spaced intervals along an axial path defined between the battery printed circuit board 182 (not shown) and the distal end 30 of the flexible backing 20. The distal wire 181 can be threaded through the plurality of holes by stitching the flexile wire as a single "thread." Other types of stitching patterns or stitching of multiple "threads" could also be used, as well as using a sewing machine or similar device to machine-stitch the distal wire 181 into place, as further described infra. Further, the path of the distal wire 181 need not be limited to a straight line from the distal to the proximal end of the flexible backing 20.

An effective ECG compression solution can reduce battery power consumption, ameliorate storage restriction, and extend monitoring time. The effectiveness of an ECG compression technique is evaluated mainly through compression ratio, degree of error loss, and execution time. The compression ratio is the ratio between the bit rate of the original signal and the bit rate of the compressed one. The error loss is the error and loss in the reconstructed data compared to non-compressed data. The execution time is the computer processing time required for compression and decompression. A lossless compressions may provide exact reconstruction of ECG data, but usually cannot provide a significant compression ratio, thus may not be a good choice when high compression ratio is required. In addition, analysis of ECG data does not require exact reconstruction; only certain feature of the ECG signal are actually important. Therefore, lossy compression, or techniques that introduce some error in the reconstructed data, is useful because lossy compression may achieve high compression ratios.

Figure 22:
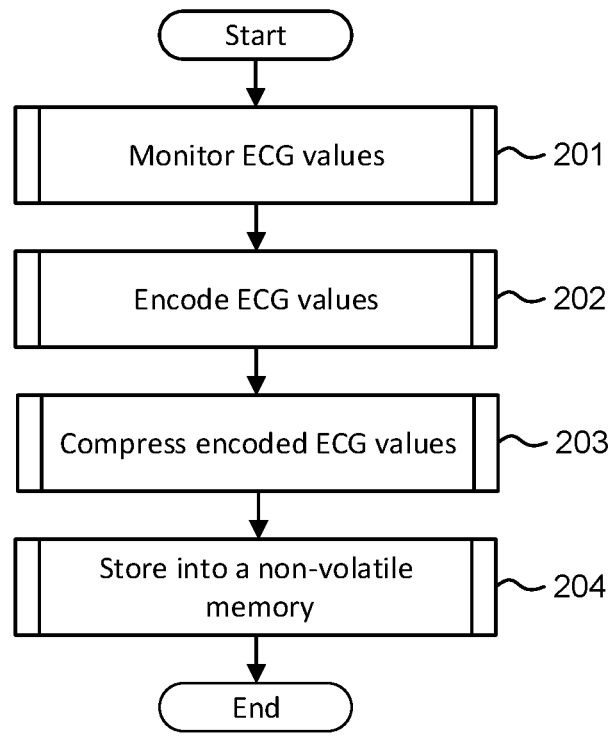
FIG. 22 is a flow diagram showing a monitor recorder-implemented method for ECG signal processing and ECG data compressing for use in the monitor recorders of FIG. 4.

The ECG signal captured by the monitor recorder 14 is compressed by the compression module 134 as part a firmware 132 located on microcontroller 61 prior to being outputted for storage, as shown in FIG. 14. FIG. 22 is a flow diagram showing a monitor recorder-implemented method for ECG signal processing and ECG data compressing for use in the monitor recorders of FIG. 4. A series of ECG signals are sensed through the front end circuit 63, which converts analog ECG signals into an uncompressed digital representation. The compressing module 134 first read the digital presentation of the ECG signals or ECG values (step 201). The compressing module 134 subsequently encodes the ECG value (step 202). This encoding step achieves one level of lossy compression and, in one embodiment, is a form of lossy compression, as further discussed infra in FIG. 23. The compressing module 134 also performs a second level of compression by further encoding and compressing the sequence of codes resulting from the encoding process of step 202 (step 203). The compressed data is stored into a non-volatile memory, such as the flash memory 62.

Figure 23:
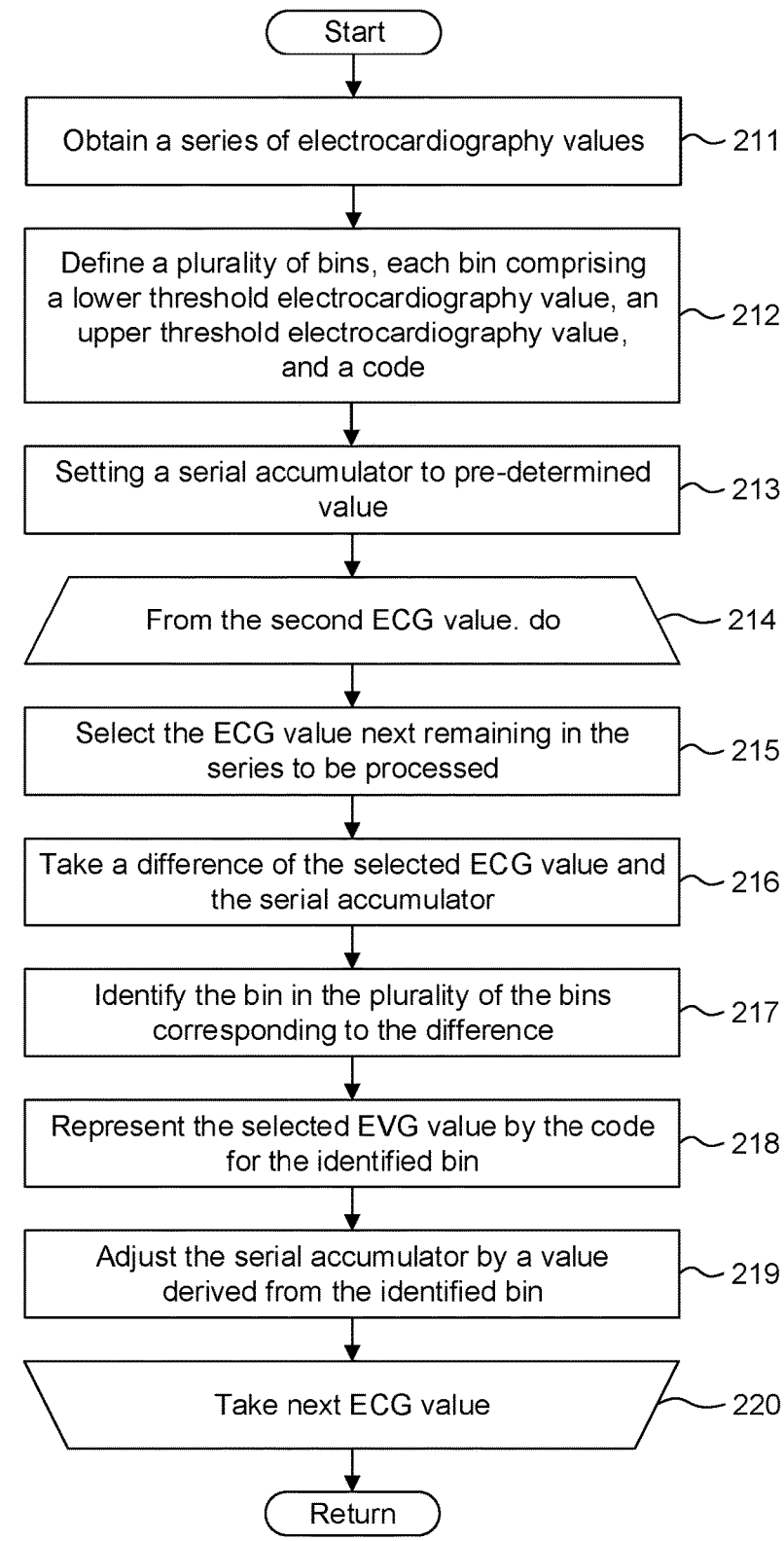
FIG. 23 is a flow diagram showing a monitor recorder-implemented method for encoding ECG values.

Monitoring ECG (step 201) is described in FIG. 12. Encoding ECG values (step 202) is performed by translating each sample data into one of codes, or encodings, further described with reference to the table in FIG. 24. By encoding ECG data in the form of a series of codes, a level of compression is achieved. FIG. 23 is a flow diagram showing a monitor recorder-implemented method for encoding ECG values. FIG. 24 is an example of a panel of codes or encodings with each code covering a range defined by a lower threshold ECG value and an upper threshold ECG value, to be referenced to during the encoding process described in FIG. 23. In one embodiment, a series of ECG values are obtained, which constitute a datastream (step 211). The series of ECG value can be one of raw electrocardiography value, processed electrocardiography value, filtered electrocardiography value, averaged electrocardiography value, or sampled electrocardiography value. The compression module 134 defines a plurality of bins, each bin comprising a lower threshold ECG value, an upper threshold ECG value, and an encoding or code (step 212). One example of such a panel of the bins is shown in the Table in FIG. 24, with the first column denoting the lower threshold ECG value, the second column denoting the upper threshold ECG value, and the third column denoting the code of a bin. An ECG data value is assigned to a corresponding bin, based upon the difference between the data value and a serial accumulator. The first serial accumulator is set to a predetermined value such as a center value of an ECG recorder (step 213), each succeeding serial accumulator is a function of a previous serial accumulator and the actual ECG reading and will be described infra. For the series of the ECG values, the following encoding steps are performed by the compression module (steps 214 to 220). These steps includes: selecting the ECG value next remaining in the series to be processed (step 215); taking a difference between the selected ECG value and the serial accumulator (step 216); identifying the bin in the plurality of the bins corresponding to the difference (step 217), which will be further described infra; representing the selected ECG value by the encoding for the identified bin (218); and adjusting the serial accumulator by a value derived from the identified bin (step 219). Through this process, each ECG value is represented, or encoded, by one of the bins. As a result, one level of data compression is achieved since the limited number of bins requires less storage space compared to the actual ECG data values.

Several ways of executing the step 217, i.e., identifying the bin in the plurality of the bins corresponding to the difference between the selected ECG value and the serial accumulator, or assigning a difference between the selected ECG value and the serial accumulator to a proper bin. In one embodiment, a difference is assigned to a bin when the difference lies between the lower threshold ECG value and the upper threshold ECG value of the bin. There are two options to assign a bin when a difference between the selected ECG value and the serial accumulator falls onto the lower threshold ECG value or the upper threshold ECG value of a bin. In one option, a bin is identified when the difference is equal to or larger than the lower threshold ECG value and smaller than the upper threshold ECG value of the identified bin. In the other option, a bin is identified when the difference is larger than the lower threshold ECG value and equal to or smaller than the upper threshold ECG value of the identified bin.

During the step 219, the value derived from the identified bin can be the lower threshold ECG value, the higher threshold ECG value, or a number derived from the lower threshold ECG value, upper threshold ECG value, or both. The derivation can be an addition or subtraction of the lower or upper threshold ECG value by a constant number or an offset. The derivation can also be an adaptive process wherein the offset may be adjusted to input ECG data, and varies from one bin to another bin.

Converting ECG values into a limited numbers of codes facilitate a further compression step which will be described infra. Some data error loss is introduced by the encoding process; however, proper bin setup minimizes the ECG data error loss and preserves useful data essential for accurate diagnosis, including P-wave signal. The number of codes and the lower and upper threshold ECG value of the codes are determined to achieve both efficient encoding and sufficient data reconstruction, especially for P-wave signals. The number of codes and the lower and upper threshold ECG value of the codes are flexible and can be adjusted to adapt to ECG data input and storage space. In one embodiment, the number of the bins are chosen from $2^3$ to $2^{10}$. A higher number of bins usually results in less ECG data error loss but more storage space and battery power use.

The proper demarcation of upper and lower thresholds also reduces error loss and contributes to accurate reconstruction of ECG value and graph shape. The number of bins and the thresholds for these bins are carefully selected to keep essential information of the ECG signals and filter away non-essential information, with a special emphasis to accurately representing the P-wave. Normally, each successive bin continues forward from a previous bin so as to cover a contiguous range of electrocardiography values. In one embodiment, the size of the bins, i.e., the interval between the higher threshold ECG value and the lower threshold ECG value, are not equal thought the contiguous range; instead, areas of high frequency calls for a smaller size of bins. The size of the bins is partly determined by the frequency of the ECG values falling into the bin.

In one embodiment, $2^4=16$ bins are used, as described with reference to the table in FIG. 24 where the lower threshold ECG value and upper threshold ECG value for each bin are also provided. This setup provides minimum error loss and a significant compression ratio, among other considerations. The first, second, and third columns represent the lower threshold ECG value, the upper threshold ECG value, and the coding of the bins. The bin that an ECG data will fall into depends on the difference between the raw ECG data value and corresponding serial accumulator compared to the range that the bin covers. If an ECG raw data falls into a particular bin, the raw ECG data can be represented by the code of the bin. In this example, the codes are encoded with a four-bit storage space, with one bit to encode sign and three bits to encode magnitude. Similar, up to 32 codes can be encoded with a five-bit storage space, with one bit to encode sign and 4 bits to encode magnitude.

The minimum (Min) and maximum (Max) values in the table in FIG. 24 defines an inclusive range of ECG values for each ECG code. An input ECG value that falls within the range defined by a pair of Min and Max values is encoded by the code appearing in the third column in the table. The Min and Max ranges can be the same for all of the bins or can be tailored to specific ranges of ECG values, to emphasize higher or lower density. For example, the range of Min and Max values 5,001-50,000 corresponding to code +7 is low density and reflects the expectation that few actual ECG values exceeding 5001 µV will occur. As a further example, the Min and Max ECG value ranges can be evenly defined throughout, or be doubled in each of the successive bins. In one embodiment, the number of bins is selected to be a power of two, although a power of two is not strictly required, particularly when a second stage compression as further described below with reference to FIG. 26. In a further embodiment, the density of the Min and Max value can be adjusted to enhance ECG signal detection, such as the P-wave signal, as further described infra beginning with reference to FIG. 28.

FIG. 25 is an example illustrating the encoding and compression scheme in accordance with method and parameters as described with reference to in FIGS. 23 and 24. The first three ECG values of an ECG datastream, 12000, 11904, and 12537, are shown in column I to show a recursive process. Remaining values are omitted since they are processed through the same recursive process. The initial ECG value, 12000, is equivalent to the center value of the ECG recorder. The initial serial accumulator is assigned to the center value of the ECG recorder, 12000. The difference between the initial ECG value to the initial serial accumulator is 0, which falls within the lower and upper threshold of bin 0. Thus the initial ECG value is encoded with the code 0. 12000 is transferred to next row as the serial accumulator for next ECG value. The next ECG value is 11904. The difference between the next ECG value and the serial accumulator for the second value is 11904−12000=−96. The difference of −96 falls into the bin with the code of −3, where the lower threshold of the bin is −41 and the upper threshold of the bin is −150. Thus, the second ECG value is encoded with the code of −3, which is the bin identification. For the purpose of decoding the second value, an encoder first refers to the assigned bin, which is bin −3; the encoder then reads the lower threshold ECG value of the assigned bin −3, which is −41; and the encoder finally add the lower threshold ECG value of the assigned bin to the decoded value of the first ECG value, which is 12000, to arrive at a decoded value of 11959. The decoded value 11959 in turn serves as the serial accumulator for the next ECG value, in this case the next ECG value is the third one of 12537. The difference between the third value and its corresponding serial accumulator is 12537−11959=578. This difference, 578, falls into the bin with a code of +5, which has a lower threshold ECG value of 301 and upper threshold ECG value of 1500. Thus the third ECG value is encoded with the code of +5. The third ECG value is decoded by adding the lower threshed ECG value of the assigned bin +5, which is 301, to the decoded value of second ECG value, which is 11959, to arrive at the decoded value of 12260. The decoded value of 12260 in turn will serve as the serial accumulator for the next ECG value. The encoding process continue until the last reading is taken. The encoder keeps track of the accumulated encoded value as the encoding process progresses along.

The encoding process is also a lossy compression process that encodes raw ECG signals with a finite number of codes. This process captures essential information while achieving significant data compression. In one embodiment, another compressing step is performed. The other compression step may be performed independently. The other compression step may also be performed on top of the encoding process described above to achieve a higher level compression than one step alone. The second compression step can be a lossless compression performed on the codes from the first step. In one embodiment, the compression ratio of the second compression is in the range of 1.4 to 1.6, increasing the data storage capacity of a non-volatile memory by more than 41-66%. In another embodiment, the compression ratio of the second compression is in excess of 1.6, increasing the data storage capacity of a non-volatile memory by more than 66%. Thus, the combination of the lossy compression and the lossless compression serves to achieve both high fidelity of the ECG signal preservation and high compression ratio, which translate into increased data storage capacity and reduced power consumption for the ambulatory electrocardiography monitor, resulting in extended wear time of the monitor.

Figure 26:
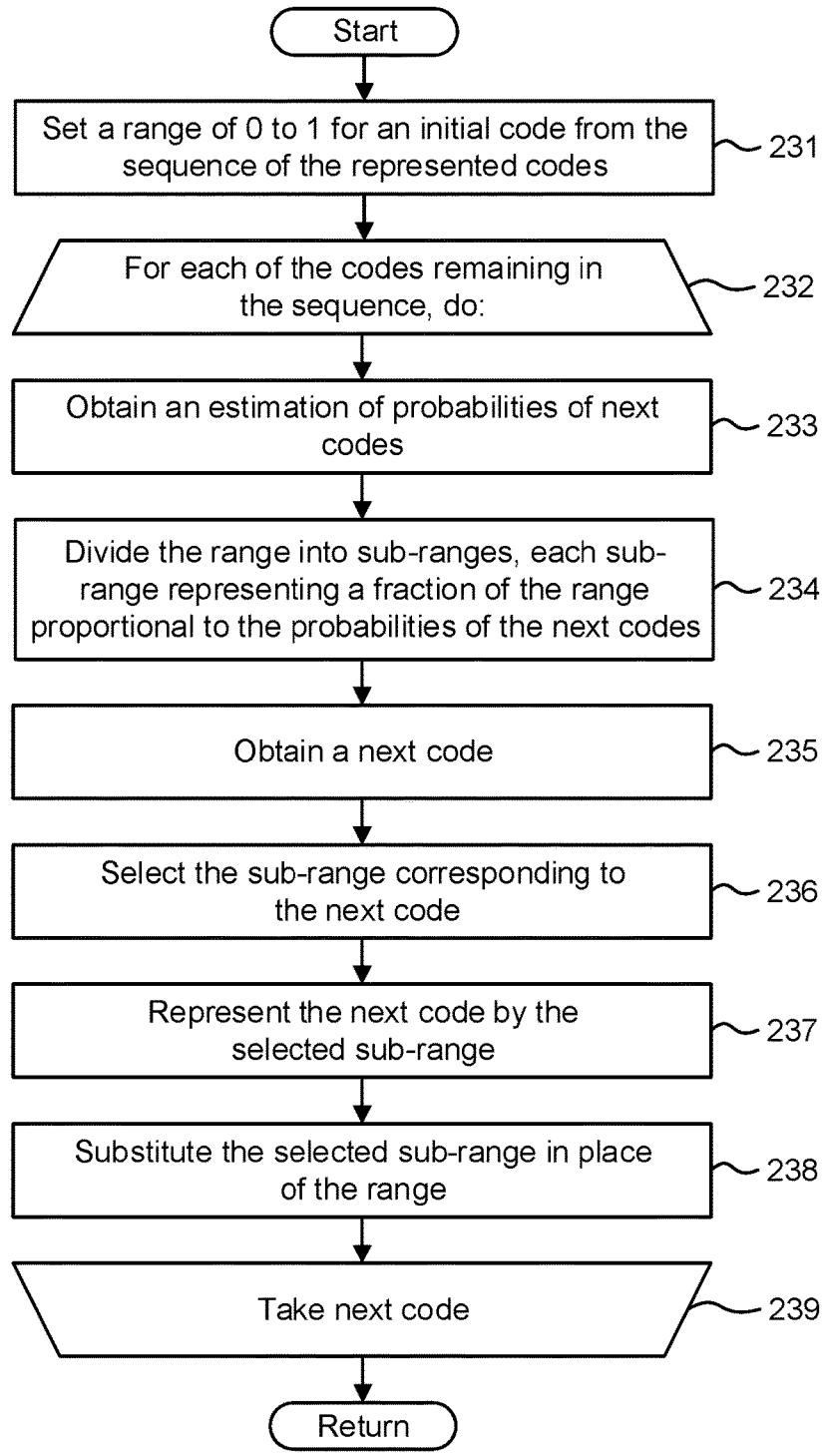
FIG. 26 is a flow diagram showing a monitor recorder-implemented method for further compressing the encodings.

In one embodiment, the second compression is effected by encoding a sequence of codes obtained from the first compression into a single number between 0 and 1, with frequently used codes using fewer bits and not-so-frequently occurring codes using more bits, resulting in reduced storage space use in total. FIG. 26 is a flow diagram showing a monitor recorder-implemented method for further compressing the codes. A sequence of the codes corresponding to the series of the ECG values is provided to the compressing module 134. The compressing module 134 set a range of 0 to 1 to an initial sequence of the codes (step 231). The compressing module 134 further performs recursive steps of assigning each successive codes into a sub-range within a previous range according to the probabilities of the codes appearing after a code (steps 232-239). The compressing module 134 obtains an estimation of probabilities of next codes, given a current code (step 233). Several variations of calculating and adjusting the probabilities of the next codes will be described infra. The compressing module 134 divides the range of the current code into sub-ranges, each sub-range representing a fraction of the range proportional to the probabilities of the next codes (step 234). These sub-ranges are contiguous and sequential. The compressing module 134 reads the next code (step 235) and selects the sub-range corresponding to the read next code (step 236). The read next code is represented, or encoded, by the corresponding sub-range (step 237). The sub-range corresponding to the read next code is assigned to be the range for the code next to the read next code (step 238), and the range is further divided into sub-ranges with each sub-range representing a fraction of the range proportional to the probabilities of codes next to the read next code (step 39). In this way, each code in the sequence of the codes is represented by, or encoded through, its location within a sub-range through a recursive process. During the recursive process, strings of codes represented by the selected sub-ranges are encoded into part of the single number between 0 and 1 and can be periodically or continually stored into the non-volatile memory, can be stored on-demand or as-needed, or can be queued up and stored en masse upon completion of the process. One example of the non-volatile memory is the flash memory 62.

The compressing module 134 uses a statistical model to predict what the next code is, given a current encoding (step 233). In one embodiment, a total of 16 codes or bin numbers are used, thus the statistical model uses 16 tables, one for each current code. Within each table, numeric possibilities for 16 possible next codes given the particular current code are generated. In one embodiment, the probabilities of the next codes can be calculated from sample ECG values. In another embodiment, the probabilities of the next codes can be modified by ECG data including recorded ECG data and data presently recorded. In still another embodiment, the probabilities of next codes can be adaptive, i.e, adjusted or varied along the recursive compression steps. Finally, in yet another embodiment, the compressing module 134 may use a statistical model to arrive at the estimation of probabilities of next codes, given two or more consecutive preceding codes. When two consecutive preceding codes are used, 16×16=256 different pairs of consecutive codes are possible. The compressing module 134 generates 256 tables, each tables containing numeric possibilities for 16 possible next codes given a particular pair of previous codes. When three consecutive preceding codes are used, 16×16×16=4096 different trios of consecutive codes are possible. The compressing module 134 generates 4096 tables, each tables containing numeric possibilities for 16 possible next codes given a particular trio of previous codes. Using two or more consecutive preceding codes further enhances compression ratio compared to using one preceding code, but also demands more processing power from the microcontroller.

In some situations, minimum amplitude signals may be masked by or become indistinguishable from noise if the granularity of the encoding is too coarse. Such overly inclusive encoding can occur if the Min and Max ECG values in the table in FIG. 24 for an ECG code define a voltage range that is too wide. The resulting ECG signal will appear "choppy" and uneven with an abrupt (and physiologically inaccurate and potentially misleading) slope. FIG. 28 is a graph 280 showing, by way of example, an ECG waveform 281 with a low amplitude signal that has been degraded by compression artifacts. The amplitude 283 of the P-wave 282 is significantly smaller than the amplitude 285 of the QRS-complex 281. In addition, the QRS-complex 281 has a pronounced slope with a relatively smooth peak and valleys. Due to compression artifacts 256 caused by an over-wide range of the Min and Max ECG values used in encoding, the P-wave 282 has a stepped appearance. As a result, important signal content is lost due to too few values being used to encode the P-wave 282.

Figure 29:
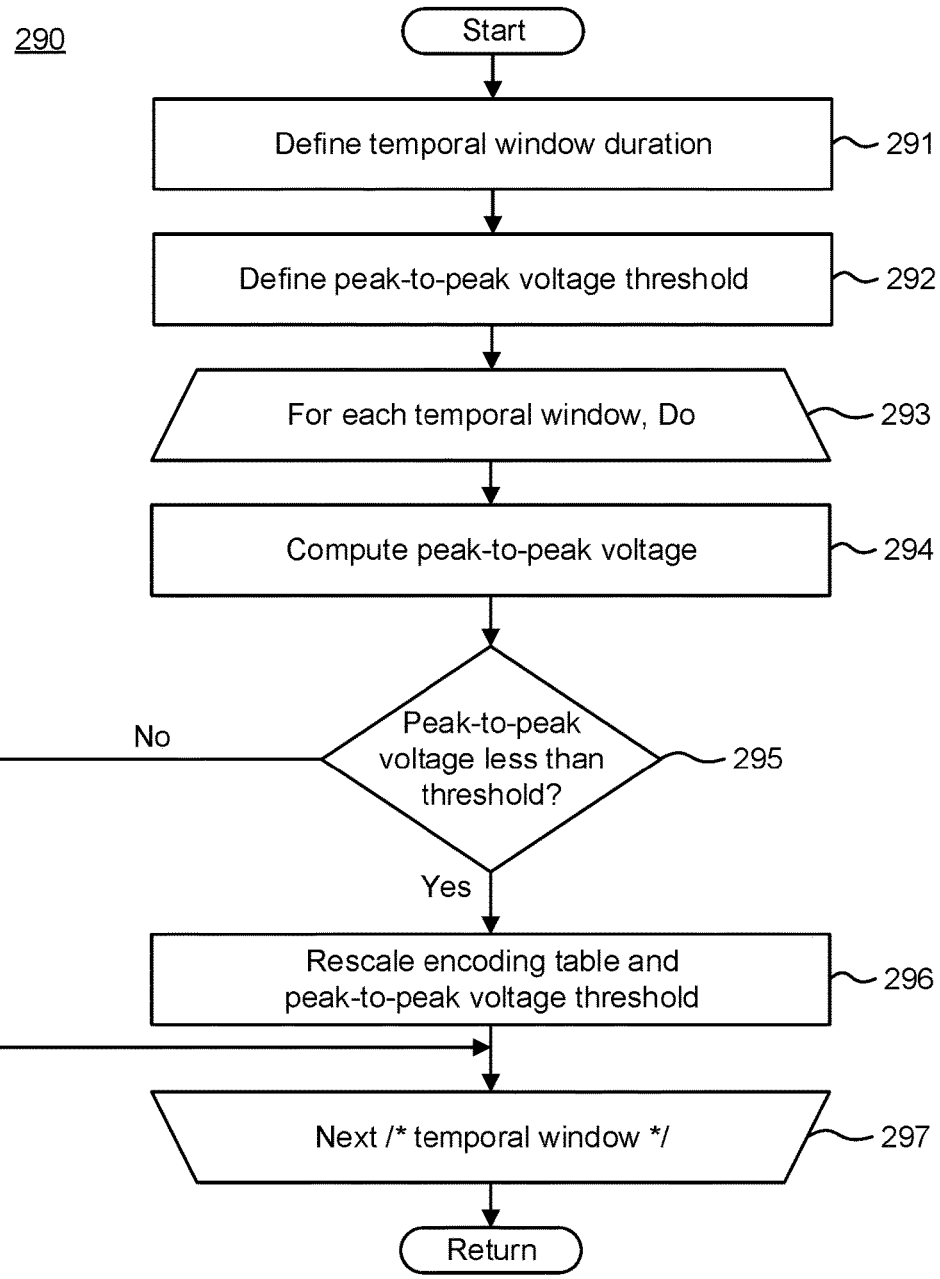
FIG. 29 is a flow diagram showing a routine for providing rescalable encoding.

In a further embodiment, the density of the Min and Max values can be adjusted to optimize cardiac signal detail capture by enhancing low amplitude ECG signal detail, especially as implicit in the shape of the slope of the P-wave. FIG. 29 is a flow diagram showing a routine 290 for providing rescalable encoding. Rescaling is generally performed during data compression values (step 202 in FIG. 24) as raw ECG signals are being stored in a monitor recorder's memory. As initial steps, a duration for each temporal window and an acceptable peak-to-peak voltage threshold are respectively defined (steps 291 and 292). In one embodiment, a temporal window duration of about five seconds, which could be plus or minus some amount, and an acceptable peak-to-peak voltage threshold of about 1.0 mV are used, although other temporal window durations and acceptable peak-to-peak voltage thresholds are possible. The raw ECG signal is then iteratively processed as successively-occurring temporal windows (steps 293-296). For each temporal window (step 293), the peak-to-peak voltage is computed (step 294). If the peak-to-peak voltage is less than the acceptable threshold (step 295), the encoding table and acceptable peak-to-peak voltage threshold are rescaled by a factor of 0.5 (step 296). Other scaling factors are possible. ECG signal processing continues with the new encoding (step 297).

In addition, if, while encoding samples (step 202 in FIG. 24), the desired difference between the peak-to-peak voltage and the acceptable peak-to-peak voltage threshold exceeds the Max value in the entry in the table in FIG. 24 for the ECG code to which the ECG value being encoded corresponds, the encoding table and acceptable peak-to-peak voltage threshold are rescaled by a factor of 2.0, until the Max value in that table entry is larger than the ECG value being encoded. Other scaling factors are possible. When the table is scaled in this way, a message is inserted into the data indicating how the table has been scaled, which can be used during decompression and post-processing.

While the invention has been particularly shown and described as referenced to the embodiments thereof, those skilled in the art will understand that the foregoing and other changes in form and detail may be made therein without departing from the spirit and scope.

What is claimed is:

1. A system for providing dynamic gain over non-noise electrocardiographic data with the aid of a digital computer, comprising:
    a download station configured to execute code comprising:
        a value module configured to obtain a time series of a plurality of voltage values that comprises a digital representation of a raw electrocardiography ("ECG") signal recorded by an ambulatory monitor recorder;
        a mark module configured to mark one or more segments of the ECG signal as noise, each of the segments comprising a plurality of the values, based on a difference between a maximum one and a minimum one of the values within that segment; and
        an analysis module configured to analyze further segments not marked as noise each of the segments comprising a plurality of the values, and to determine a gain factor for all of the values in the analyzed further segments based on the analysis.

2. A system according to claim 1, wherein the analysis comprises determining a maximum and a minimum values in each of the non-noise segments and determining a statistical correlation based on the maximum and the minimum values of each of the further segments.

3. A system in accordance with claim 1, further comprising:
    a filter module configured to apply a filter during the marking of the noise selected from the group comprising a high pass filter, a low pass filter, an amplitude change filter, and a zero-crossings filter.

4. A system according to claim 1, wherein each of the further segments falls within temporal windows of a same duration.

5. A system according to claim 4, wherein the duration is long enough to capture at least one heart beat.

6. A system according to claim 1, the download station further comprising:
    a bridging module configured to bridge the further segments to create a continuous ECG signal for display.

7. A system according to claim 6, the download station further comprising:
    a storage module configured to store the time series; and
    a display module configured to display a representation of the raw ECG signal upon receiving a user command.

8. A method for providing dynamic gain over non-noise electrocardiographic data with the aid of a digital computer, comprising the steps of:
    obtaining a time series of a plurality of voltage values that comprises a digital representation of a raw electrocardiography ("ECG") signal recorded by an ambulatory monitor recorder;
    marking one or more segments of the ECG signal as noise, each of the segments comprising a plurality of the values, based on a difference between a maximum one and a minimum one of the values within that segment; and analyzing further segments not marked as noise each of the segments comprising a plurality of the values; and determining a gain factor for all of the values in the analyzed further segments based on the analysis, wherein the steps are performed by a suitably-programmed computer.

9. A method according to claim 8, wherein the analysis comprises determining a maximum and a minimum values in each of the non-noise segments and determining a statistical correlation based on the maximum and the minimum values of each of the further segments.

10. A method in accordance with claim 8, further comprising the step of:

applying a filter during the marking of the noise selected from the group comprising a high pass filter, a low pass filter, an amplitude change filter, and a zero-crossings filter.

11. A method according to claim 8, wherein each of the further segments falls within temporal windows of a same duration.

12. A method according to claim 11, wherein the duration is long enough to capture at least one heart beat.

13. A method according to claim 8, further comprising:

bridging the further segments to create a continuous ECG signal for display.

14. A method according to claim 13, the further comprising:

storing the time series; and displaying a representation of the raw ECG signal upon receiving a user command.

15. An ambulatory adjustable encoding monitor recorder, comprising:

a memory configured to store a plurality of codes and a plurality of electrocardiographic values associated with each of the codes;

a microcontroller configured to sense electrocardiographic values during a sequence of temporal windows and to process the electrocardiographic values within each of the windows, the microcontroller further configured to:

calculate a mathematical relationship between a maximum one and a minimum one of the electrocardiographic values in each of the temporal windows;

compare each of the relationships to an at least one threshold;

based on the comparison of the relationship for at least one of the windows, adjust the plurality of the electrocardiographic values associated with each of the codes;

encode each of the electrocardiography values within that window with one of the codes based on the adjusted plurality of the electrocardiographic values associated with that code; and write each of the codes into a sequence in the memory of the monitor recorder.

16. A monitor recorder according to claim 15, wherein the adjusted plurality of the electrocardiographic windows are used for the processing of at least one of the windows following that window.

17. A monitor recorder according to claim 15, the microcontroller further configured to:

define a desired value for the mathematical correlation; and calculate a difference between the desired value and the at least one threshold; and adjust the plurality of the electrocardiographic values based on the difference.

18. A monitor recorder according to claim 15, the microcontroller further configured to:

define a length of each of the temporal windows and an acceptable peak-to-peak threshold associated with that window, wherein the at least one threshold comprises the peak-to-peak threshold.

19. A monitor recorder according to claim 18, wherein the peak-to-peak threshold comprises 1.0 mv.

20. A monitor recorder according to claim 15, the microcontroller further configured to:

associate a message regarding at least one of the adjustments with the codes stored in the memory.

* * * * *